US011752286B2

(12) United States Patent
Delangre et al.

(10) Patent No.: US 11,752,286 B2
(45) Date of Patent: *Sep. 12, 2023

(54) REMOTE RESPIRATORY THERAPY DEVICE MANAGEMENT

(71) Applicant: RESMED INC., San Diego, CA (US)

(72) Inventors: Peter Delangre, Sydney (AU); Paul Frederick Birchall, Sydney (AU); Dawn Rosemary Churchill, Sydney (AU); Graham Stephen Cutcliffe, Sydney (AU); Christopher John Roberts, San Diego, CA (US); Chinmayee Somaiya, Sydney (AU); Bradley Scott Templeton, Sydney (AU); Wendall Eric Trull, San Diego, CA (US); Matthew Scott Tyler, San Diego, CA (US)

(73) Assignee: ResMed Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/407,741

(22) Filed: Aug. 20, 2021

(65) Prior Publication Data

US 2022/0072248 A1  Mar. 10, 2022

Related U.S. Application Data

(63) Continuation of application No. 15/313,345, filed as application No. PCT/AU2015/050280 on May 27, 2015, now Pat. No. 11,116,924.

(30) Foreign Application Priority Data

May 27, 2014  (AU) ................... 2014901999

(51) Int. Cl.
*A61M 16/06*  (2006.01)
*A61M 16/16*  (2006.01)
(Continued)

(52) U.S. Cl.
CPC ............ *A61M 16/024* (2017.08); *A61B 5/00* (2013.01); *A61M 16/0051* (2013.01);
(Continued)

(58) Field of Classification Search
CPC ............ A61M 16/024; A61M 16/0051; A61M 16/0057; A61M 16/107; A61M 16/16;
(Continued)

(56) References Cited

U.S. PATENT DOCUMENTS 4,782,832 A   11/1988  Trimble et al.
7,942,824 B1   5/2011  Kayyali et al.
(Continued)

FOREIGN PATENT DOCUMENTS

EP    1684172 A1   7/2006
EP    2471568 A2   7/2012
(Continued)

OTHER PUBLICATIONS

M. Blount et al., Remote health-care monitoring using Personal Care Connect, 2007, [Retrieved on Mar. 14, 2023], Retrieved from the internet: <URL: https://ieeexplore.ieee.org/stamp/stamp.jsp?tp=&arnumber=5386592> 19 Pages (95-113) (Year: 2007).*
(Continued)

*Primary Examiner* — Anibal Rivera
(74) *Attorney, Agent, or Firm* — Botos Churchill IP Law LLP

(57) ABSTRACT

A system and method for updating patient devices is disclosed. The patient devices may include respiratory therapy devices that operate in accordance with instruction sets, such as software or firmware. A server may maintain a database of configuration data indicating the versions of the software and firmware that is currently installed on the patient devices. The server may also transmit updated instructions from over a network, including a wireless network. Particu-
(Continued)

lar patient devices may be selected for updating based on the configuration data. Upon performing an update a patient device may transmit configuration data to the server.

21 Claims, 15 Drawing Sheets

(51) Int. Cl.
| | |
|---|---|
| *A61M 16/08* | (2006.01) |
| *A61M 16/00* | (2006.01) |
| *A61B 5/00* | (2006.01) |
| *G16H 40/40* | (2018.01) |
| *A61M 16/10* | (2006.01) |
| *G16H 20/40* | (2018.01) |
| *G16H 40/67* | (2018.01) |
| *G16H 10/60* | (2018.01) |
| *G16H 40/63* | (2018.01) |
| *G06F 8/65* | (2018.01) |
| *G16H 40/60* | (2018.01) |
| *G06F 8/61* | (2018.01) |
| *G16H 20/10* | (2018.01) |

(52) U.S. Cl.
CPC ....... *A61M 16/0057* (2013.01); *A61M 16/107* (2014.02); *A61M 16/1055* (2013.01); *A61M 16/16* (2013.01); *A61M 2205/3553* (2013.01); *A61M 2205/3584* (2013.01); *A61M 2205/50* (2013.01); *A61M 2205/52* (2013.01); *A61M 2205/84* (2013.01); *A61M 2209/01* (2013.01); *A61M 2209/04* (2013.01); *G06F 8/61* (2013.01); *G06F 8/65* (2013.01); *G16H 10/60* (2018.01); *G16H 20/10* (2018.01); *G16H 20/40* (2018.01); *G16H 40/40* (2018.01); *G16H 40/60* (2018.01); *G16H 40/63* (2018.01); *G16H 40/67* (2018.01); *Y02A 90/10* (2018.01)

(58) Field of Classification Search
CPC .......... A61B 5/00; G16H 20/40; G16H 40/67; G16H 20/10; G16H 40/40; G16H 40/63; G16H 40/60; G16H 10/60; G06F 8/65; G06F 8/61

See application file for complete search history.

(56) References Cited

U.S. PATENT DOCUMENTS

| | | | |
|---|---|---|---|
| 8,726,266 | B2 | 5/2014 | Kiaie |
| 8,806,473 | B2 | 8/2014 | Birtwhistle et al. |
| 9,424,020 | B2 | 8/2016 | Borges et al. |
| 9,594,875 | B2 | 3/2017 | Arrizza |
| 10,089,443 | B2 | 10/2018 | Miller et al. |
| 2001/0034617 | A1 | 10/2001 | Kimata |
| 2004/0138536 | A1 | 7/2004 | Carlson et al. |
| 2005/0065817 | A1* | 3/2005 | Mihai .................... A61B 5/411 705/2 |
| 2005/0283198 | A1* | 12/2005 | Haubrich ............ A61N 1/37282 607/30 |
| 2006/0085404 | A1 | 4/2006 | Kusunoki |
| 2007/0135866 | A1 | 6/2007 | Baker et al. |
| 2007/0136098 | A1 | 6/2007 | Smythe et al. |
| 2007/0197878 | A1 | 8/2007 | Shklarski |
| 2008/0028386 | A1 | 1/2008 | Nagamine et al. |
| 2008/0033508 | A1 | 2/2008 | Frei et al. |
| 2008/0221644 | A1 | 9/2008 | Vallapureddy et al. |
| 2009/0018623 | A1 | 1/2009 | Levinson et al. |
| 2009/0044808 | A1 | 2/2009 | Guney et al. |
| 2009/0054937 | A1 | 2/2009 | Severin et al. |
| 2009/0058635 | A1 | 3/2009 | Lalonde et al. |
| 2009/0107494 | A1 | 4/2009 | Freitag et al. |
| 2009/0157202 | A1 | 6/2009 | Roberts et al. |
| 2009/0229610 | A1 | 9/2009 | Oates et al. |
| 2010/0000534 | A1 | 1/2010 | Kooij et al. |
| 2010/0313105 | A1 | 12/2010 | Nekoomaram et al. |
| 2011/0073107 | A1 | 3/2011 | Rodman et al. |
| 2011/0179405 | A1 | 7/2011 | Dicks et al. |
| 2011/0289497 | A1 | 11/2011 | Kiaie |
| 2012/0291783 | A1 | 11/2012 | Peiris et al. |
| 2013/0036210 | A1 | 2/2013 | Birtwhistle |
| 2013/0036414 | A1 | 2/2013 | Birtwhistle et al. |
| 2013/0104120 | A1 | 4/2013 | Arrizza |
| 2013/0193041 | A1 | 8/2013 | Rohde |
| 2013/0231711 | A1 | 9/2013 | Kaib |
| 2013/0310726 | A1 | 11/2013 | Miller et al. |
| 2013/0346108 | A1 | 12/2013 | Kamen et al. |
| 2014/0025392 | A1 | 1/2014 | Chandrasenan |
| 2014/0055233 | A1 | 2/2014 | Vetrivel et al. |
| 2014/0102454 | A1 | 4/2014 | Paul et al. |
| 2014/0102455 | A1 | 4/2014 | D'Angelo |
| 2014/0114678 | A1 | 4/2014 | Moyer et al. |
| 2014/0150791 | A1 | 6/2014 | Birnkrant et al. |
| 2014/0180711 | A1 | 6/2014 | Kamen |
| 2014/0188516 | A1* | 7/2014 | Kamen .................. G16H 40/63 705/3 |
| 2014/0195639 | A1 | 7/2014 | Kamen et al. |
| 2014/0276571 | A1* | 9/2014 | Ludolph ................ G16H 20/17 604/151 |
| 2015/0039047 | A1 | 2/2015 | Parker |
| 2015/0059006 | A1 | 2/2015 | White |
| 2015/0112717 | A1 | 4/2015 | Saleh et al. |
| 2015/0199192 | A1 | 7/2015 | Borges et al. |
| 2015/0199485 | A1 | 7/2015 | Borges |
| 2016/0274162 | A1 | 9/2016 | Freeman et al. |
| 2016/0331952 | A1 | 11/2016 | Faltys et al. |
| 2017/0014587 | A1 | 1/2017 | Whiting et al. |
| 2017/0209718 | A1 | 7/2017 | Tanis et al. |
| 2017/0239432 | A1 | 8/2017 | Delangre et al. |
| 2019/0287668 | A1 | 9/2019 | Tiwari et al. |
| 2019/0347086 | A1 | 11/2019 | Kiaie et al. |

FOREIGN PATENT DOCUMENTS

| | | | |
|---|---|---|---|
| JP | 2002366653 | A | 12/2002 |
| JP | 2003134551 | A | 5/2003 |
| JP | 2004516562 | A | 6/2004 |
| JP | 2006085350 | A | 3/2006 |
| JP | 2006119848 | A | 5/2006 |
| JP | 2006171859 | A | 6/2006 |
| JP | 2006302174 | A | 11/2006 |
| JP | 2008033836 | A | 2/2008 |
| JP | 2009519107 | A | 5/2009 |
| JP | 2011238007 | A | 11/2011 |
| JP | 2012128571 | A | 7/2012 |
| JP | 2014038489 | A | 2/2014 |
| WO | 1998004310 | A1 | 2/1998 |
| WO | 2004073778 | A1 | 9/2004 |
| WO | 2005063328 | A1 | 7/2005 |
| WO | 2006074513 | A1 | 7/2006 |
| WO | 2006130903 | A1 | 12/2006 |
| WO | 2007035804 | A2 | 3/2007 |
| WO | 2009052560 | A1 | 4/2009 |
| WO | 2010135785 | A1 | 12/2010 |
| WO | 2010141922 | A1 | 12/2010 |
| WO | 2013017580 | A2 | 2/2013 |

OTHER PUBLICATIONS

Japanese Office Action for Japanese Patent Application No. 2020-197854, dated Nov. 26, 2021.
EP Communication dated Jun. 5, 2020 for EP Application No. 15800272.5.
Extended ESR for EP 15 80 0272 dated Dec. 15, 2017.
International Search Report and Written Opinion for Application No. PCT/AU2015/050280 dated Aug. 19, 2015.
JP Notice of Allowance for JP Application No. 2016-569746.
JP Office Action dated Jan. 28, 2020, JP Application No. 2016-569746.

(56) References Cited

OTHER PUBLICATIONS

JP Office Action dated Jul. 28, 2020. JP Application No. P2016-569746.
Lundberg Devin, et al., On the Security of Mobile Cockpit Information Systems, Nov. 3-7, 2014, [Retrieved on Apr. 28, 2021], Retrieved from the internet: <URL: https://dl.acm.org/doi/pdf/10.1145/2660267.2660375> 13 Pages (633-645) (Year: 2014).
Mohan, Apurva, et al., Cyber Security for Personal Medical Devices Internet of Things, 2014 IEEE, [Retrieved on Apr. 28, 2021]. Retrieved from the internet: <URL: https://ieeexplore.ieee.org/stamp/stamp.jsp?tp=&arnumber=6846193> 3 Pages (372-374) (Year: 2014).
West, John B, "Respiratory Physiology", Lippincott Williams & Wilkins, 9th edition published 2011.

\* cited by examiner

REMOTE RESPIRATORY THERAPY DEVICE MANAGEMENT

CROSS-REFERENCES TO RELATED APPLICATIONS

This application is a continuation of U.S. patent application Ser. No. 15/313,345 (now issued as U.S. Pat. No. 11,116,924), filed Nov. 22, 2016, which is a national phase entry under 35 U.S.C. § 371 of International Application No. PCT/AU2015/050280 filed May 27, 2015, published in English, which claims priority from Australian Provisional Patent Application No. 2014901999, filed on May 27, 2014, the disclosure of which is incorporated herein by reference.

1 BACKGROUND

1.1 (1) Field of the Technology

The present technology relates to one or more of the detection, diagnosis, treatment, prevention and amelioration of respiratory-related disorders. In particular, the present technology relates to medical devices or apparatus, their use, and updating the same.

1.2 (2) Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Some examples of respiratory disorders include: Obstructive Sleep Apnea (OSA), Cheyne Stokes Respiration (CSR), Obesity Hyperventilation Syndrome (OHS), Chronic Obstructive Pulmonary Disease (COPD), Neuromuscular Disease (NMD) or chest wall disorders.

Otherwise healthy individuals may take advantage of systems and devices to prevent respiratory disorders from arising.

1.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body by doing some or all of the work of breathing. The ventilator support is provided via a patient interface. NIV has been used to treat CSR, OHS, COPD, MD and Chest Wall disorders.

Invasive ventilation (IV) provides ventilatory support to patients that are no longer able to effectively breathe themselves and is provided using a tracheostomy tube.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

1.2.3 Systems

A treatment system may comprise a Respiratory Pressure Therapy Device (RPT device), an air circuit, a humidifier, a patient interface, and data management.

1.2.4 Patient Interface

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use and uncomfortable especially when worn for long periods of time or when a patient is unfamiliar with a system. For example, masks designed solely for aviators, mask designed as part of personal protection equipment (e.g. filter masks), SCUBA masks or for the administration of anaesthetics may be tolerable for their original application, but nevertheless be undesirably uncomfortable to be worn for extended periods of time, e.g. several hours. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, masks for delivery of nasal CPAP during sleep form a distinct field.

1.2.4.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be in appropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to affect a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris.

Another form of seal-forming portion may use adhesive to affect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

1.2.4.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

1.2.5 Respiratory Pressure Therapy (RPT) Device

One known RPT device used for treating sleep disordered breathing is the S9 Sleep Therapy System, manufactured by ResMed. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD. RPT devices have also been known as flow generators.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

RPT devices typically also include an inlet filter, various sensors and a microprocessor-based controller. A blower may include a servo-controlled motor, a volute and an impeller. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the pressure generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The controller may include data storage capacity with or without integrated data retrieval and display functions.

Table of noise output levels of prior devices (one specimen only, measured using test method specified in ISO3744 in CPAP mode at 10 cmH$_2$O).

| Device name | A-weighted sound power level dB(A) | Year (approx.) |
|---|---|---|
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 Auto Set | 26.5 | 2010 |
| S9 AutoSet with H5i Humidifier | 28.6 | 2010 |

Delivery of a flow of breathable gas without humidification may cause drying of airways. Medical humidifiers are used to increase humidity and/or temperature of the flow of breathable gas in relation to ambient air when required, typically where the patient may be asleep or resting (e.g. at a hospital). As a result, a medical humidifier is preferably small for bedside placement, and it is preferably configured to only humidify and/or heat the flow of breathable gas delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants.

The use of a humidifier with a flow generator or RPT device and the patient interface produces humidified gas that minimizes drying of the nasal mucosa and increases patient airway comfort. In addition, in cooler climates warm air applied generally to the face area in and about the patient interface is more comfortable than cold air.

Respiratory humidifiers are available in many forms and may be a standalone device that is coupled to a respiratory apparatus via an air circuit, is integrated with or configured to be coupled to the relevant respiratory apparatus. While known passive humidifiers can provide some relief, generally a heated humidifier may be used to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or RPT device, and a gas outlet adapted to be connected to an air circuit that delivers the humidified gas to the patient interface.

Heated passover humidification is one common form of humidification used with a RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 CPAP devices respectively.

Other humidifiers may also be used such as a bubble or diffuser humidifier, a jet humidifier or a wicking humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier. A wicking humidifier uses a water absorbing material, such as sponge or paper, to absorb water by capillary action. The water absorbing material is placed within or adjacent at least a portion of the air flow path to allow evaporation of the water in the absorbing material to be taken up into the air flow.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

2 BRIEF SUMMARY OF THE TECHNOLOGY

Aspects of the disclosure provide a computer implemented method for updating a patient device over a network. The method may include accessing configuration data relating to a plurality of patient devices, wherein the plurality of patient devices each implements a set of instructions. The method may also include identifying one or more patient devices, from the plurality of patient devices, having configuration data that meets one or more criteria and selecting, in the case where more than one updates are provided, an instruction update to be provided to the one or more patient devices, wherein the configuration data indicates that the instruction update is not currently installed on the one or more patient devices. The method may also include transmitting the instruction update to the one or more patient devices, as well as determining whether each of the one or more patient devices successfully installed the instruction update. In addition the configuration data may be updated for each of the one or more patient devices that successfully installed the instruction update.

In another aspect, the instruction update may include at least one of the following: data specifying a location of an instruction update file; instructions as to which component of the device should the update be applied to; schedule time for performing the update for each device; instructions on whether or not to request confirmation that the update should be applied; instructions for the update not be applied until patient treatment is stopped, if applicable; data structure and functionality enabling cancelling upgrades that have not yet occurred; batch capability to request bulk upgrades in a single operation; and an ability to check a status of these upgrades in a single operation indicating the status of the upgrades.

Selecting the one or more criteria and the instruction update may be based on received one or more transmissions from a remote computing device, e.g. the computer of a clinician or service personnel. In addition, the step of selecting the instruction update may be based on receiving input from a user of the remote computing device indicating the instruction update, from a plurality of instruction updates. Transmitting the instruction update may further include transmitting verification data, wherein the verification data is used by the patient device to verify that the received instruction update is complete. In this case the expression that the update is "complete" is also meant to indicate that the update is without corruption or alteration in any way. The instruction update may be retransmitted to each device for which it is determined that the instruction update was not successfully installed.

In accordance with yet another aspect, an indication from each of the one or more patient devices indicates that the instruction set was successfully installed, and a message may be transmitted to a computing device, wherein the message identifies successful installation of the instruction update for the one or more patient devices. The configuration data may include at least one of a) a serial number, b) a version of the set of instructions that is currently installed on the patient device, c) a hardware version, d) a region in which the patient device is being used, and e) a record of the instruction updates that have previously been successfully or unsuccessfully applied to the patient device.

In accordance with still another aspect, the plurality of patient devices may be respiratory pressure therapy devices. The configuration data may include at least one of a) a serial number, b) a version of the set of instructions that is currently installed on the patient device, and c) a hardware version. In addition, the instruction update may include a first portion and a second portion, herein a first component of the patient device operates in accordance with the first portion of the instruction update and a second component operates in accordance with the second portion of the instruction update.

In another aspect, a method for updating a device for providing medical may include accessing a first set of instructions for operation of a patient device; performing a first set of operations in accordance with the first instruction set; receiving update data from a remote computing device over a network; updating the first set of instructions in accordance with the update data so as to generate an updated set of instructions; transmitting confirmation to the remote computing device that an update of the first set of instructions has occurred; and performing a second set of operations in accordance with the updated set of instructions.

The method may also include receiving verification data, and further comprising determination of whether the received update data is complete. If the received update data is determined to be incomplete, the patient device may transmit an error notification to the remote computing device and receive a second transmission of update data.

3 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

3.1 Treatment Systems

FIG. 1a shows a system in accordance with the present technology. A patient 1000 wearing a patient interface 3000, in the form of nasal pillows, receives a supply of air at positive pressure from a RPT device 4000. Air from the RPT device is humidified in a humidifier 5000, and passes along an air circuit 4170 to the patient 1000.

3.2 Therapy 3.2.1 Respiratory System

Figure 2A:
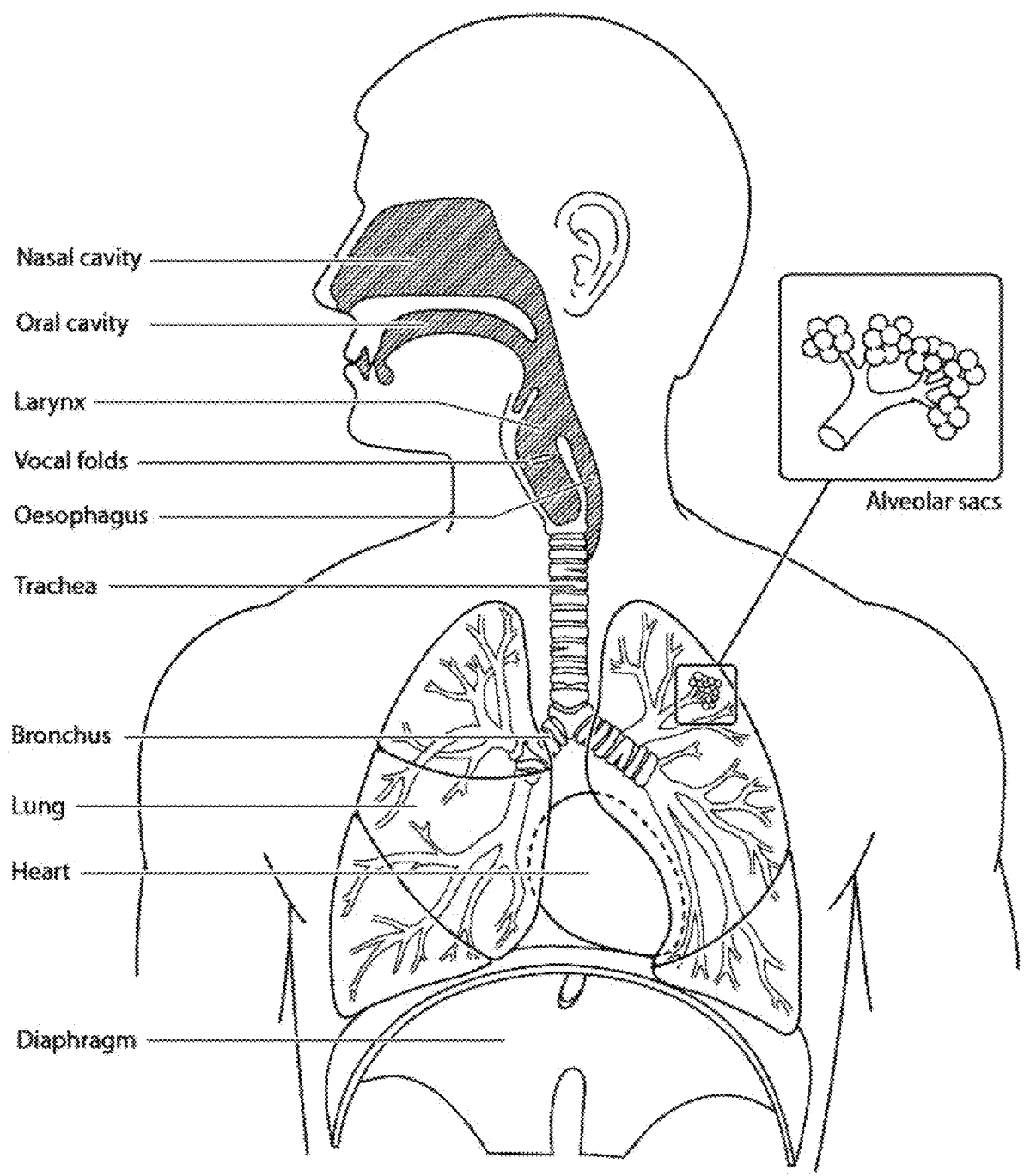

FIG. 2a shows an overview of a human respiratory system including the nasal and oral cavities, the larynx, vocal folds, oesophagus, trachea, bronchus, lung, alveolar sacs, heart and diaphragm.

Figure 2B:
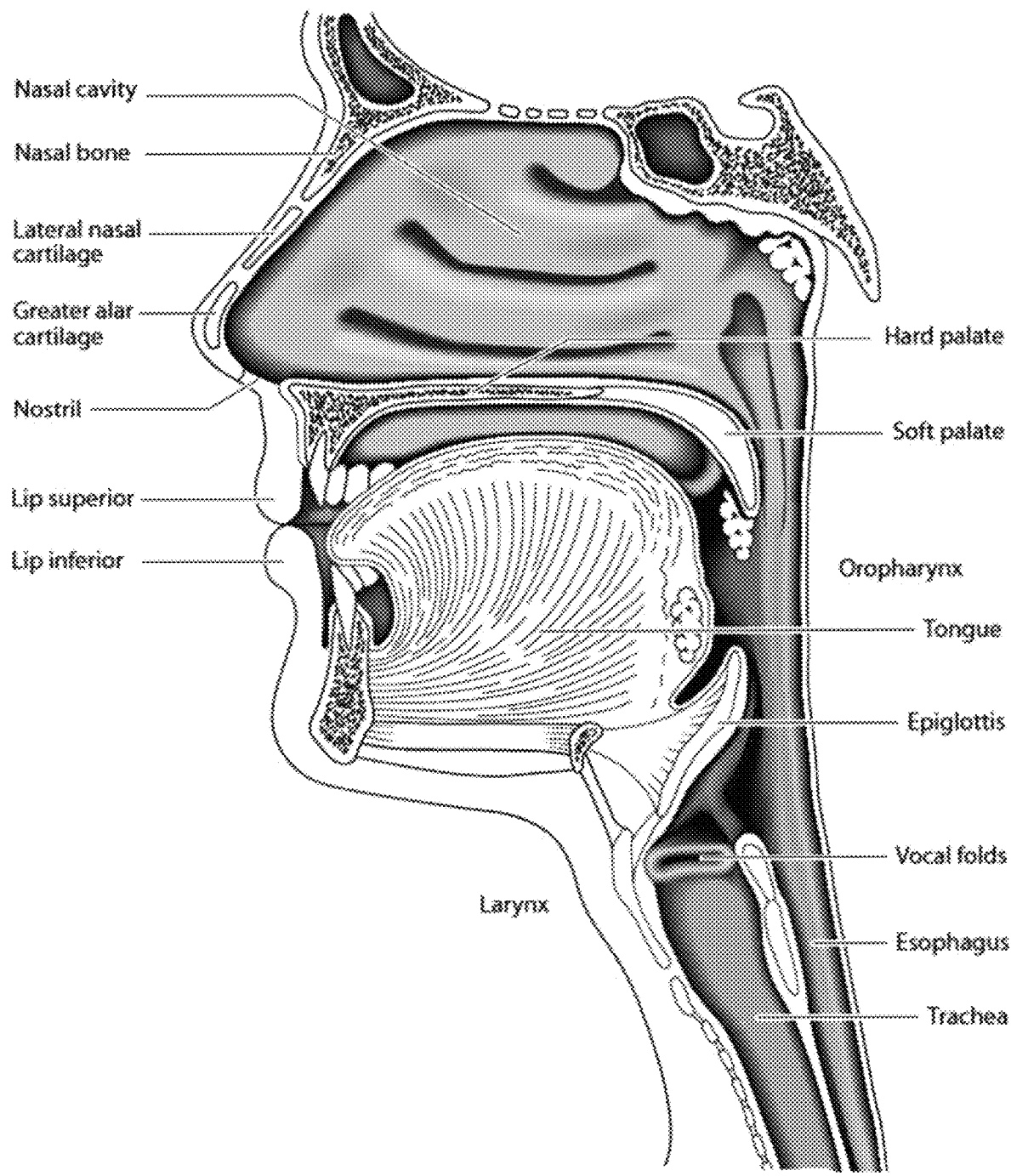

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

3.2.2 Facial Anatomy

Figure 2C:
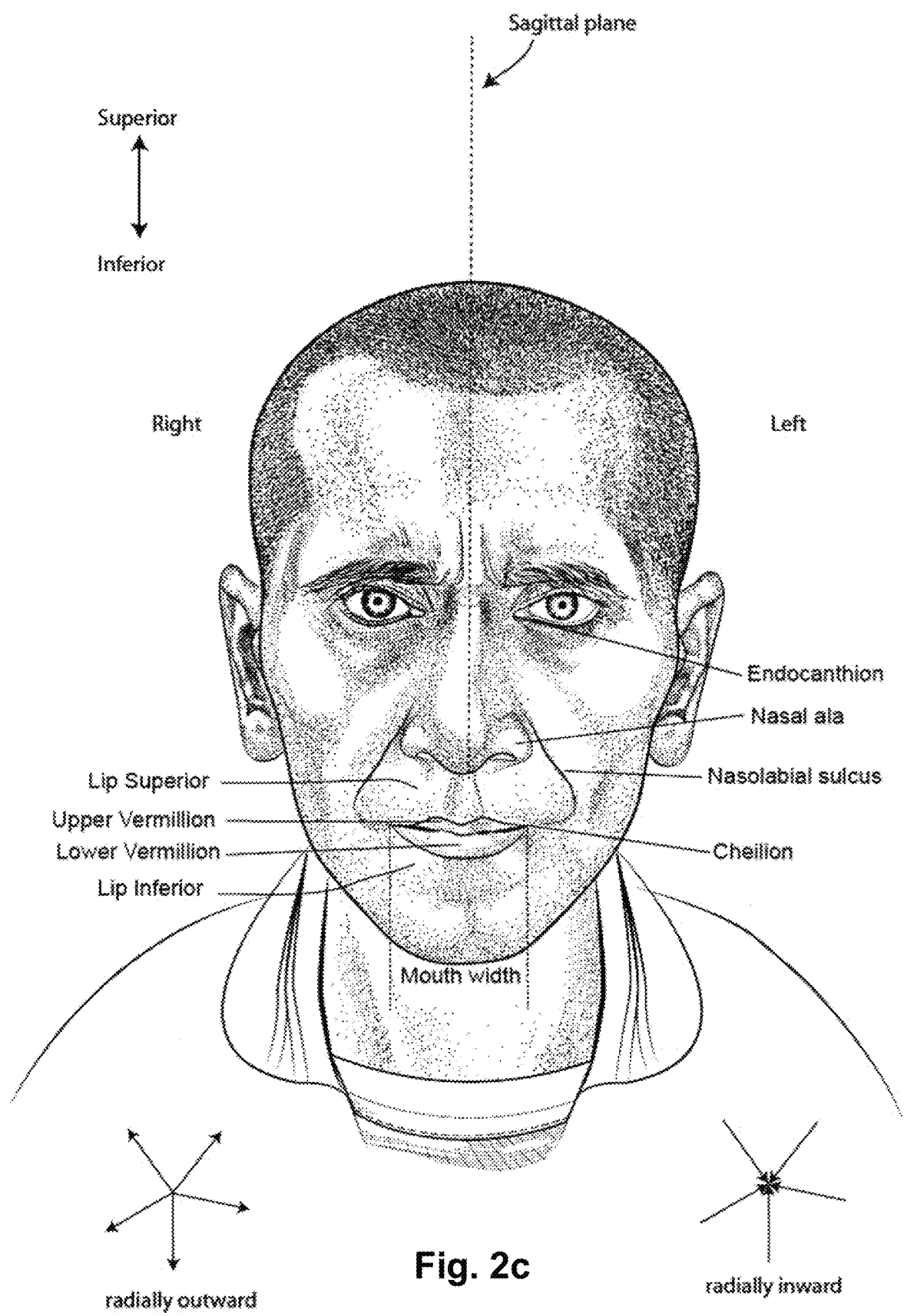

FIG. 2c is a front view of a face with several features of surface anatomy identified including the lip superior, upper vermillion, lower vermillion, lip inferior, mouth width, endocanthion, a nasal ala, nasolabial sulcus and cheilion.

3.3 Patient Interface

Figure 3A:
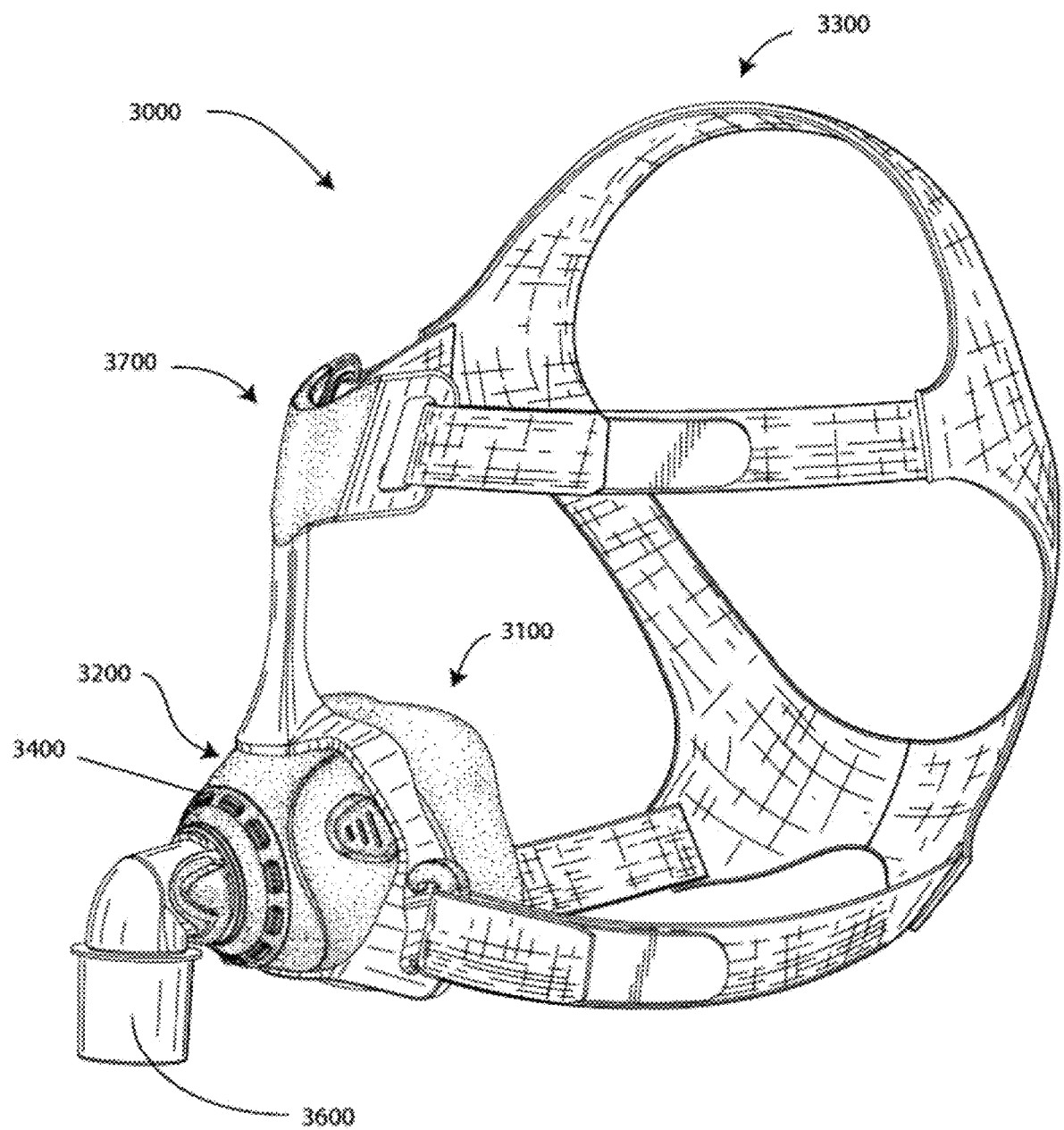

FIG. 3a shows an example of a patient interface known in the prior art.

3.4 Respiratory Pressure Therapy (RPT) Device

Figure 4A:
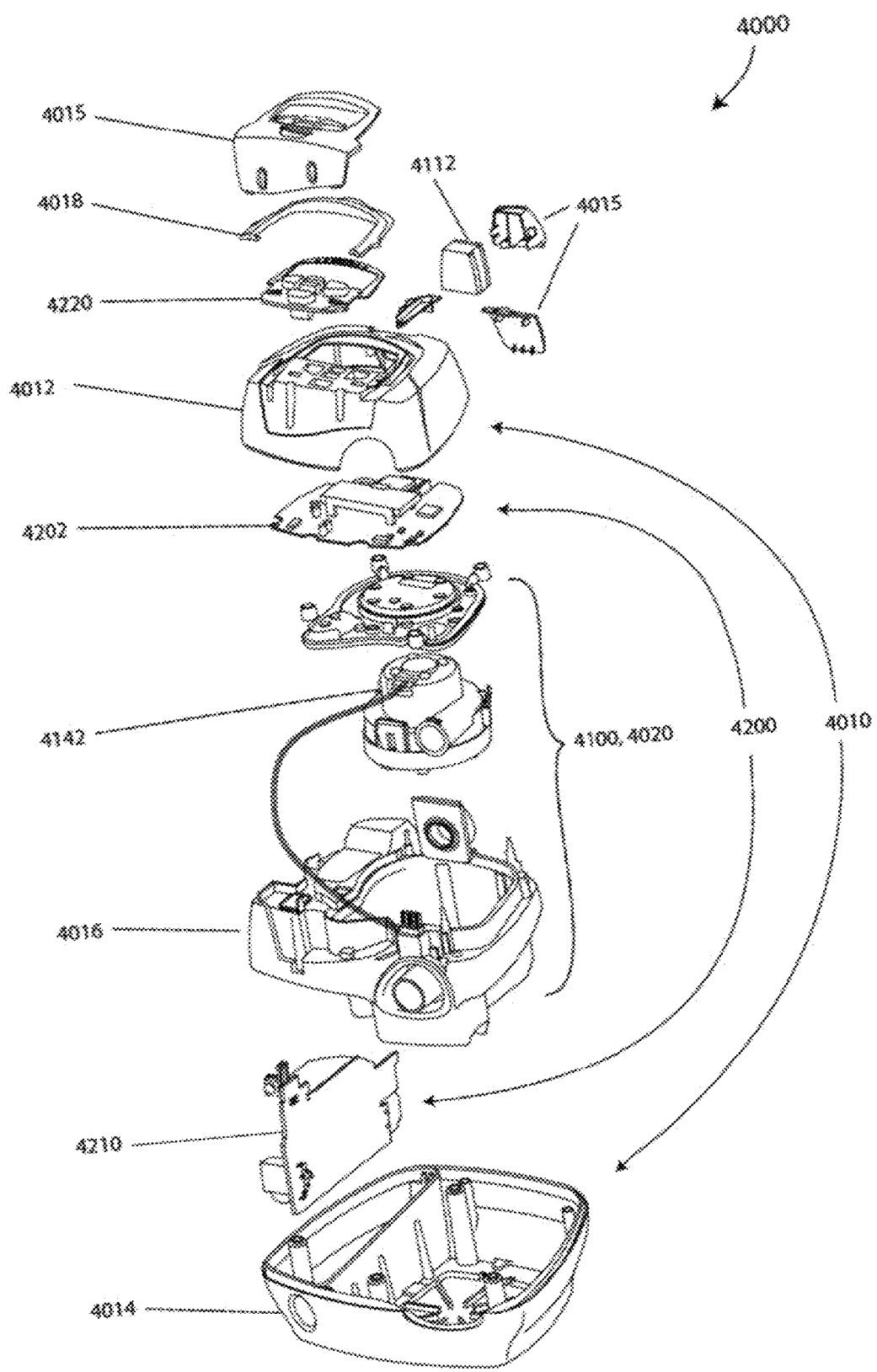

FIG. 4a shows a RPT device in accordance with one form of the present technology.

Figure 4B:
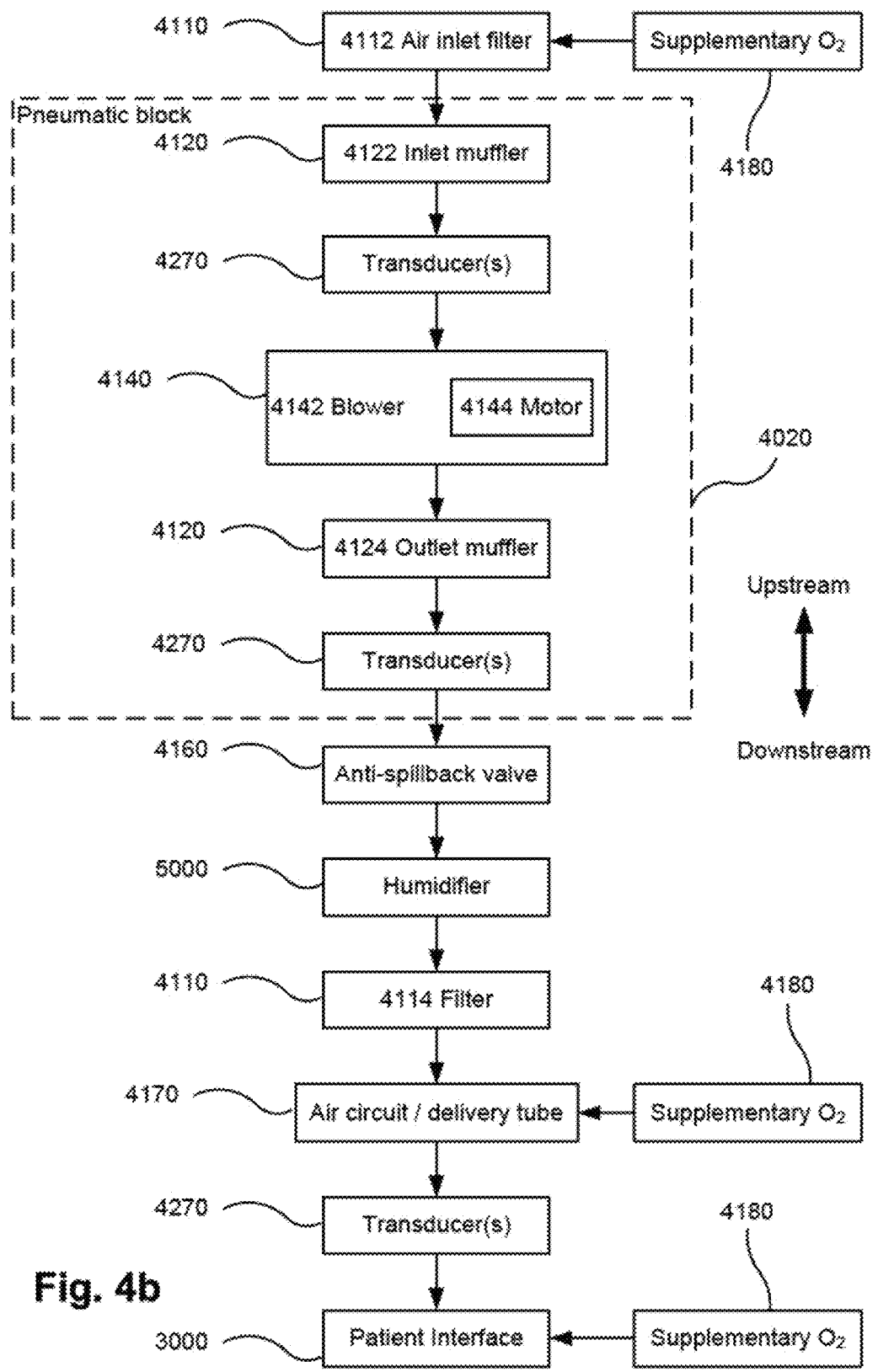

FIG. 4b shows a schematic diagram of the pneumatic circuit of a RPT device in accordance with one form of the present technology. The directions of upstream and downstream are indicated.

Figure 4C:
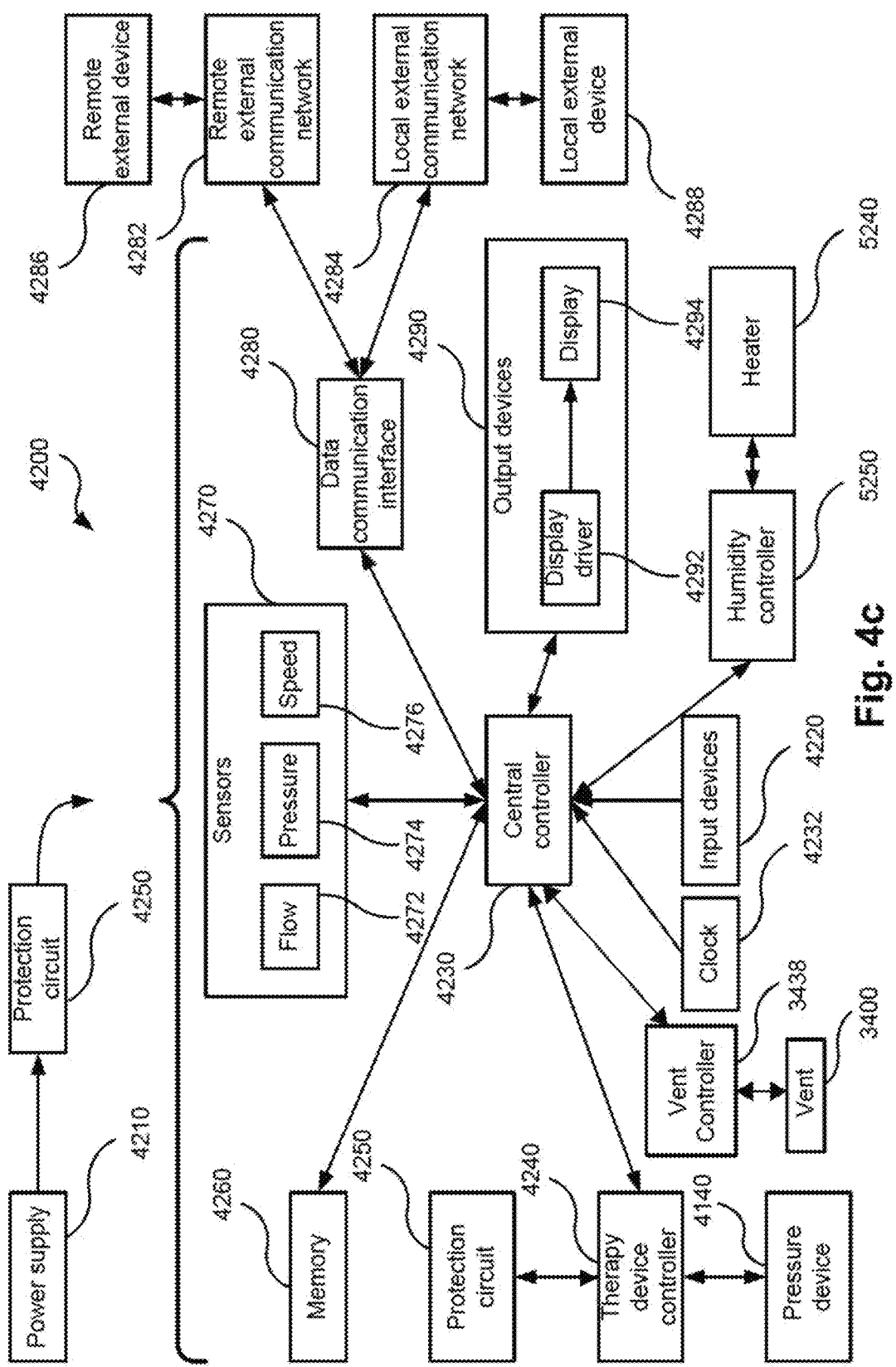

FIG. 4c shows a schematic diagram of the electrical components of a RPT device in accordance with one aspect of the present technology.

3.5 Humidifier

Figure 5A:
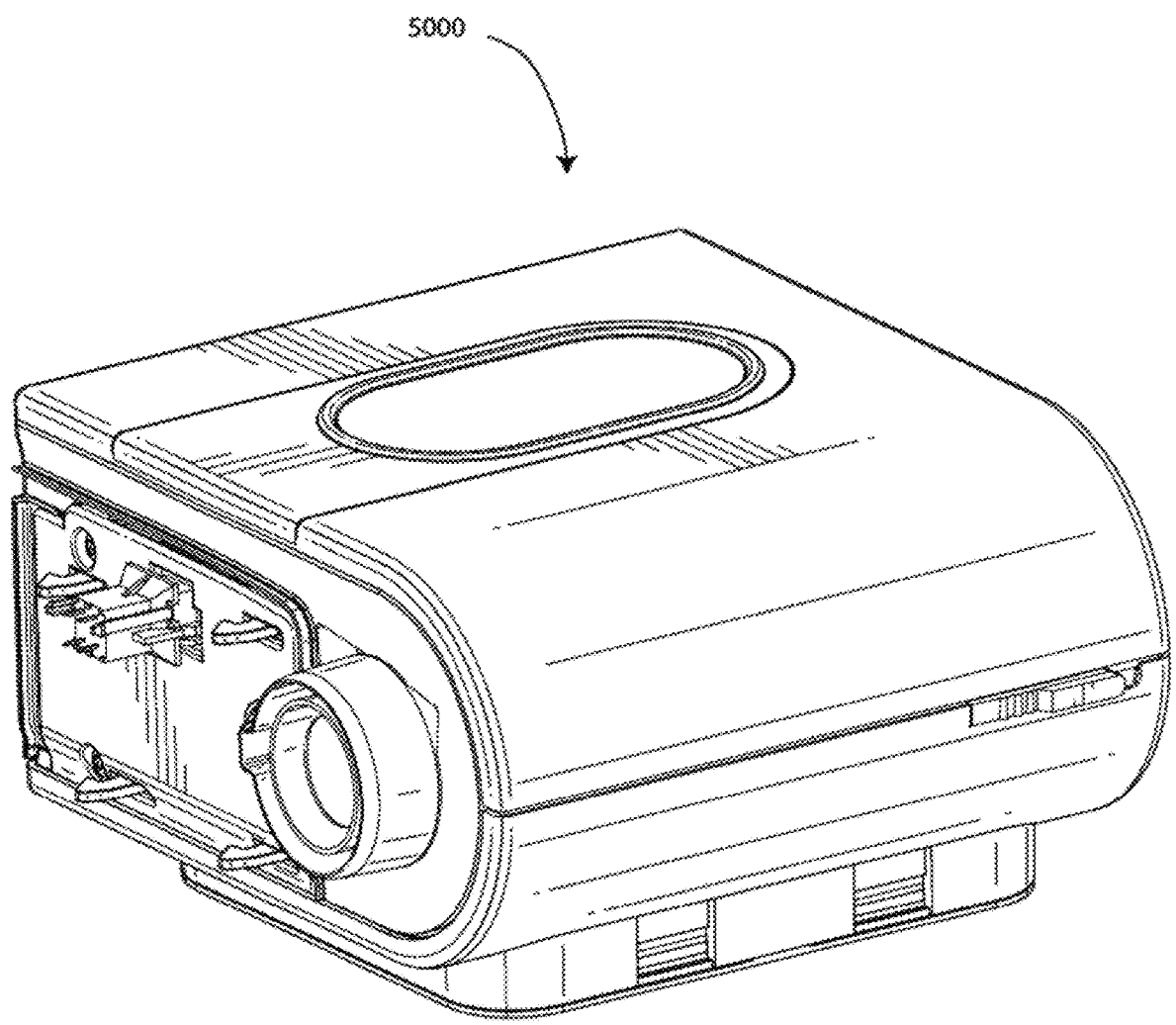

FIG. 5a shows a humidifier in accordance with one aspect of the present technology.

3.6 Breathing Waveforms

Figure 6A:
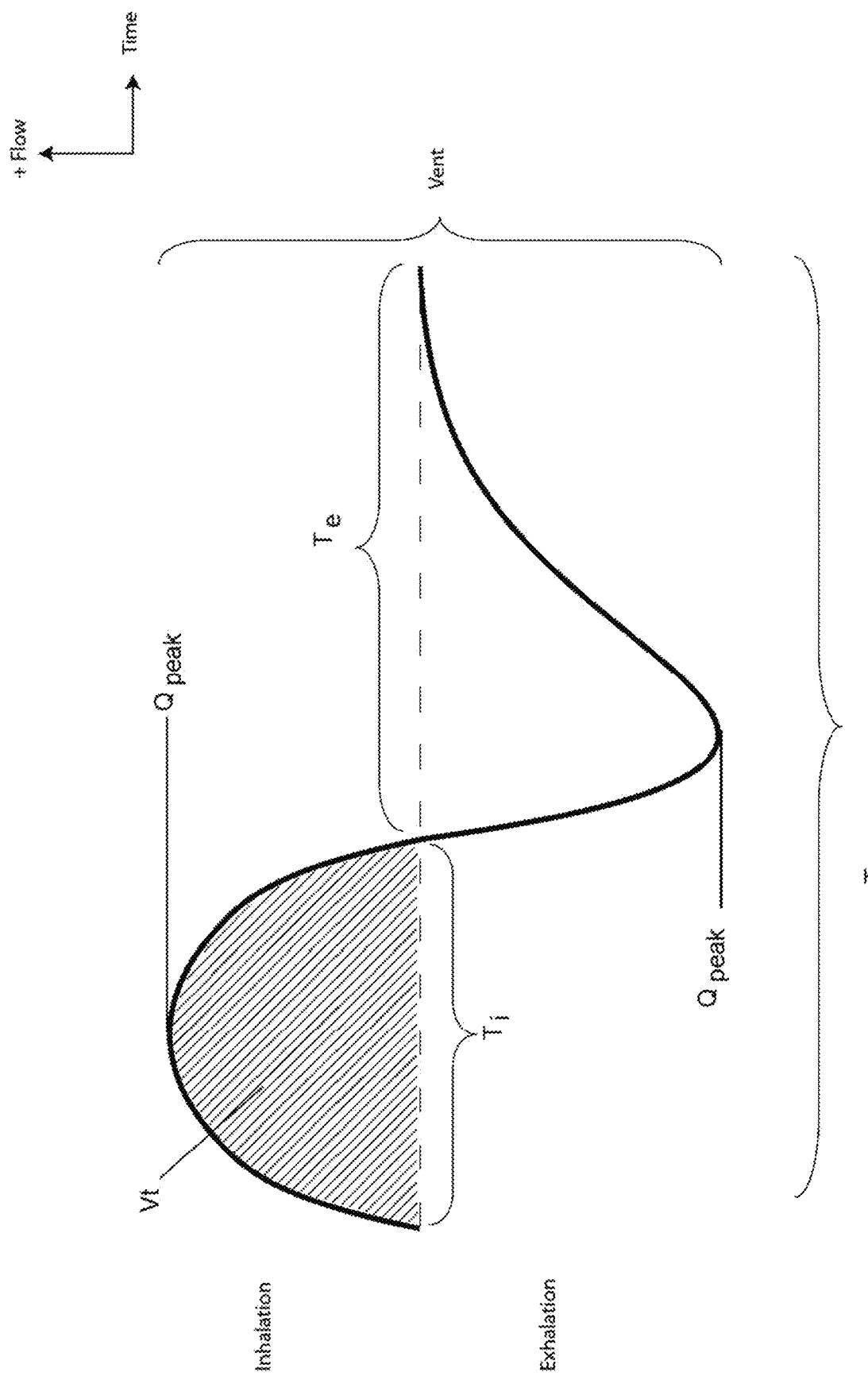

FIG. 6a shows a model typical breath waveform of a person while sleeping, the horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/s. A typical duty cycle, the ratio of Ti to Ttot is about 40%.

3.7 Data Management System

Figure 7:
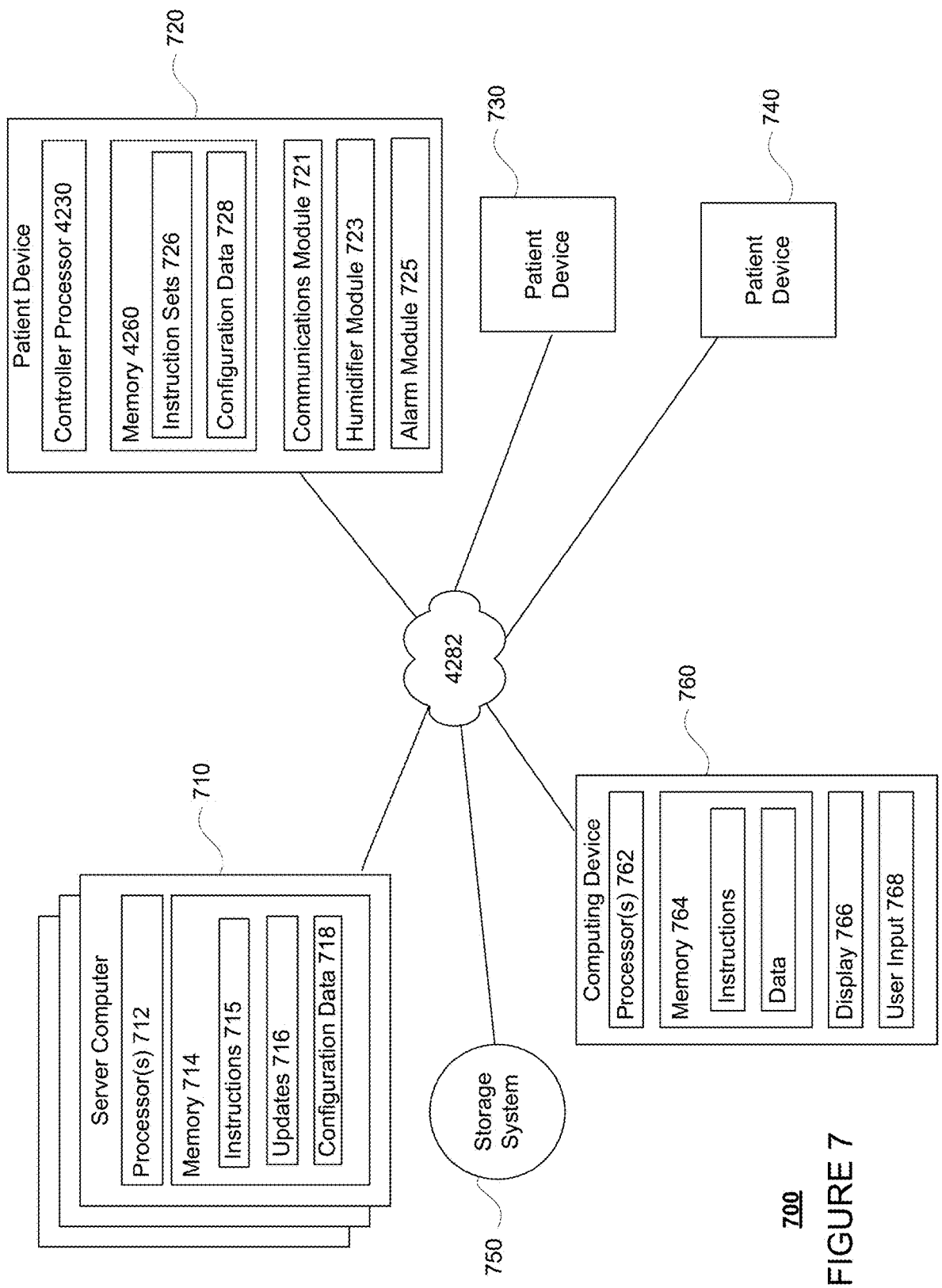

FIG. 7 shows an example communications system 700 that may be used in the collection and transmission of patient data. Each patient device 720, 730, and 740 may comprise an RPT 4000, humidifier 5000, and patient interface 3000.

Figure 8:
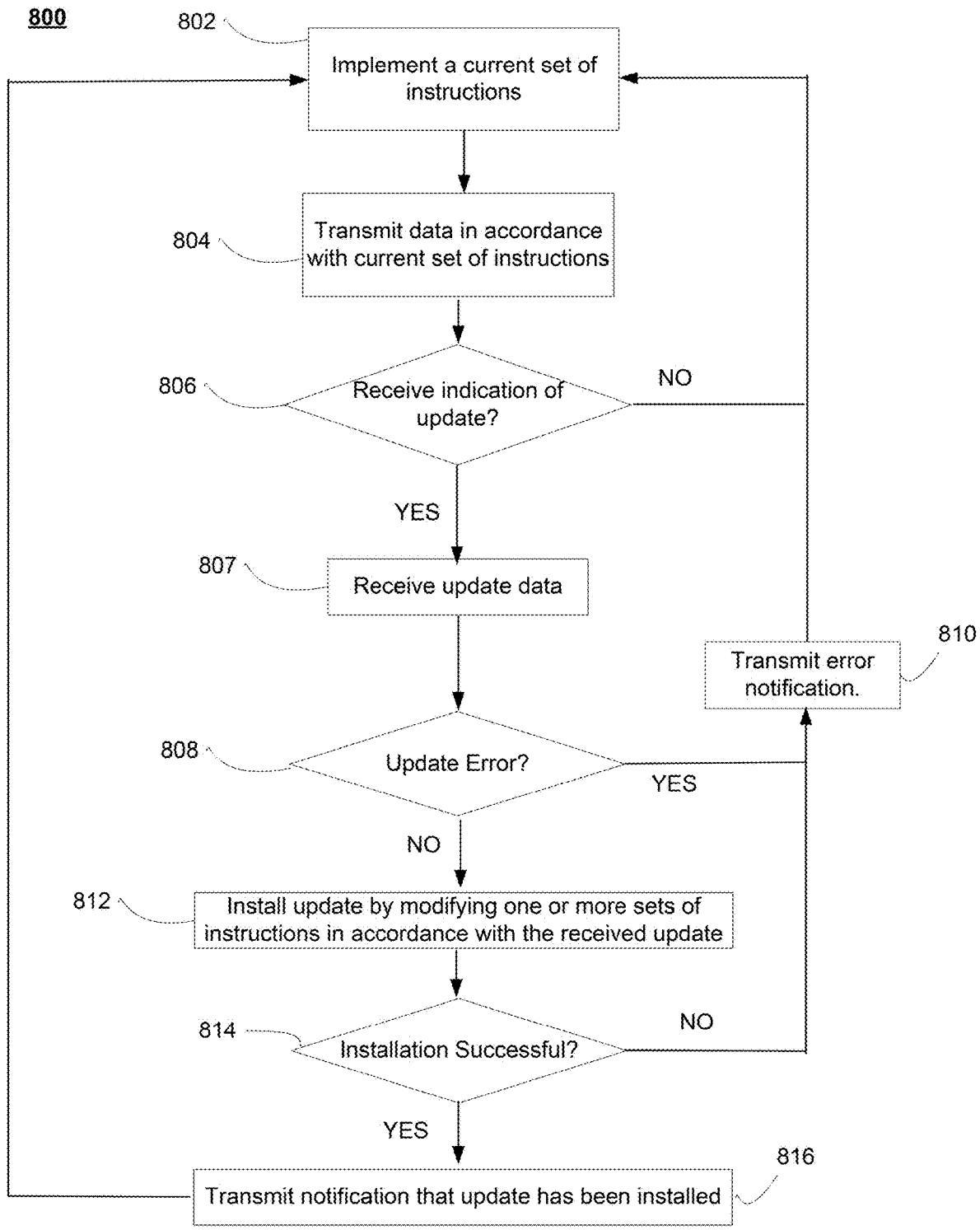

FIG. 8 shows flow diagram 800 of operations that may be performed by patient devices disclosed herein in connection with updating instruction sets that are implemented by the patient device.

Figure 9:
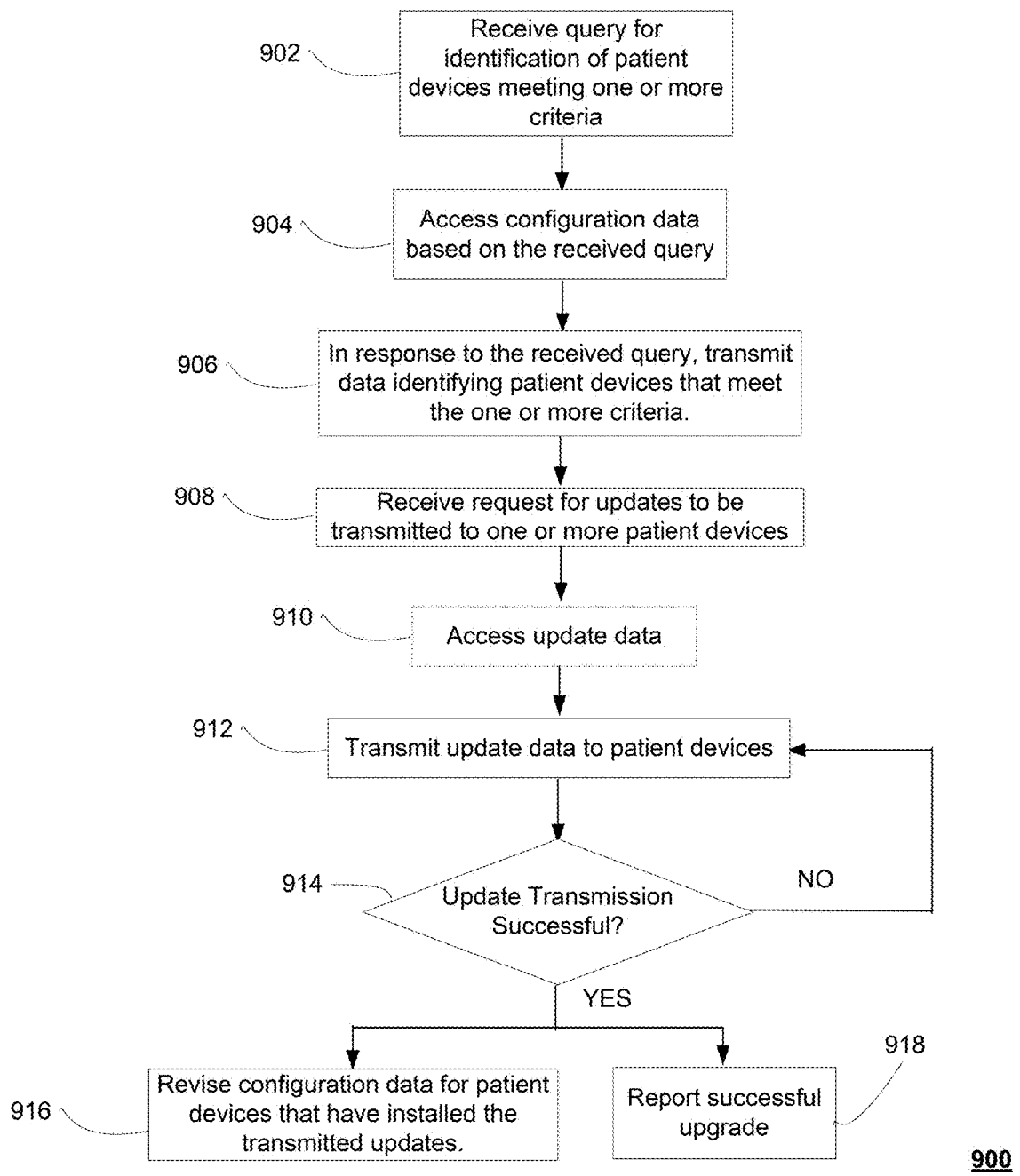

FIG. 9 shows flow diagram 900 operations that may be performed by computing devices, such as servers, disclosed herein.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

4.1 Treatment Systems

In one form, the present technology comprises apparatus for treating a respiratory disorder. The apparatus may comprise a flow generator or blower for supplying pressurised respiratory gas, such as air, to the patient 1000 via an air delivery tube leading to a patient interface 3000.

4.2 Therapy

In one form, the present technology comprises a method for treating a respiratory disorder comprising the step of applying positive pressure to the entrance of the airways of a patient 1000.

4.2.1 Nasal CPAP for OSA

In one form, the present technology comprises a method of treating Obstructive Sleep Apnea in a patient by applying nasal continuous positive airway pressure to the patient.

4.3 Patient Interface 3000

A non-invasive patient interface 3000 in accordance with one aspect of the present technology comprises the following functional aspects: a seal-forming structure 3100, a plenum chamber 3200, a positioning and stabilising structure 3300, a vent 3400 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.3.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. Preferably the sealing flange comprises a relatively thin member with a thickness of less than about 1 mm, for example about 0.25 mm to about 0.45 mm, that extends around the perimeter 3210 of the plenum chamber 3200. Support flange may be relatively thicker than the sealing flange. The support flange is disposed between the sealing flange and the marginal edge of the plenum chamber 3200, and extends at least part of the way around the perimeter 3210. The support flange is or includes a spring-like element and functions to support the sealing flange from buckling in use. In use the sealing flange can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

4.3.2 Plenum Chamber 3200

Preferably the plenum chamber 3200 has a perimeter 3210 that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. Preferably the seal-forming structure 3100 extends in use about the entire perimeter 3210 of the plenum chamber 3200.

Figure 1A:
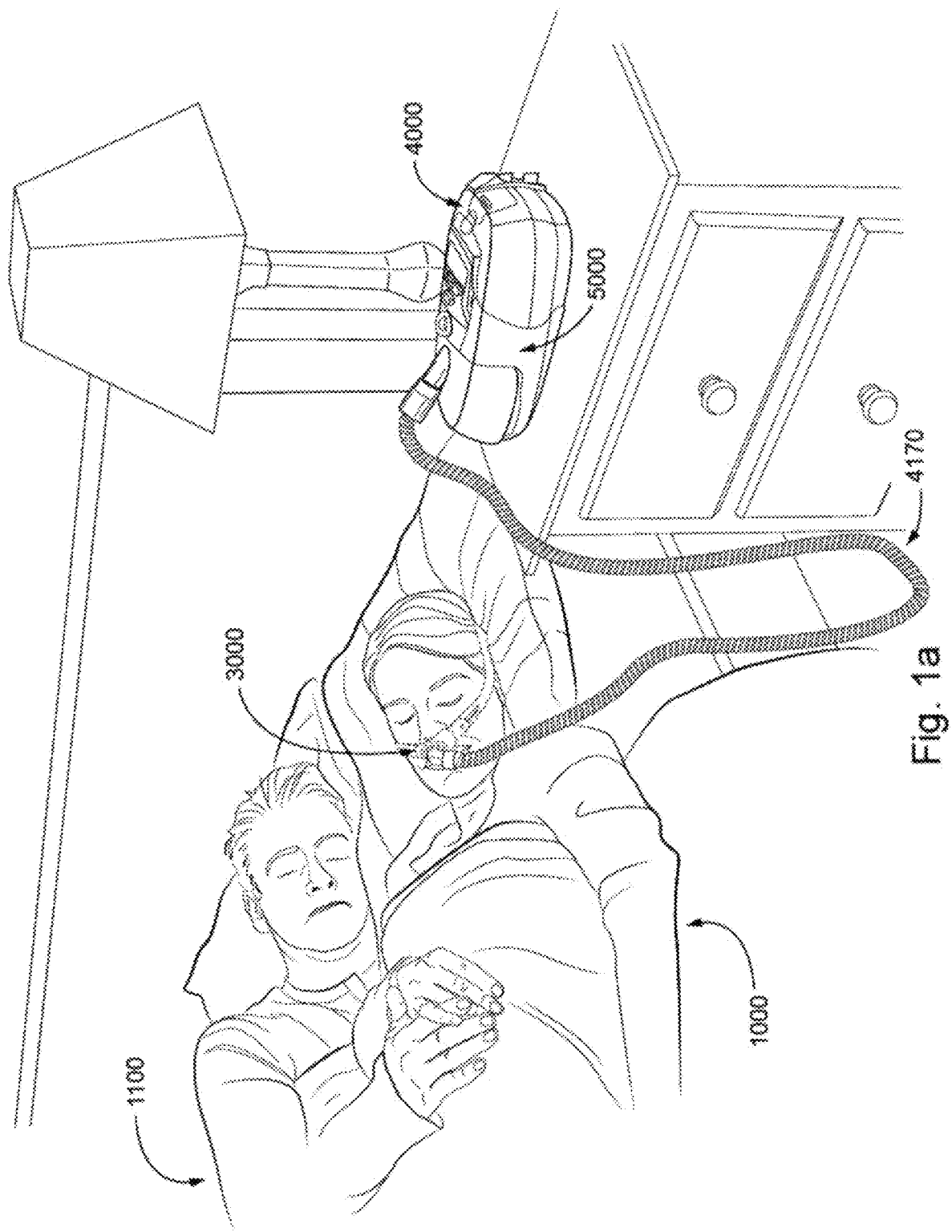
FIG. 1b shows a system including a patient 1000 wearing a patient interface 3000, in the form of a nasal mask, receives a supply of air at positive pressure from a RPT device 4000. Air from the RPT device is humidified in a humidifier 5000, and passes along an air circuit 4170 to the patient 1000.
FIG. 1c shows a system including a patient 1000 wearing a patient interface 3000, in the form of a full-face mask, receives a supply of air at positive pressure from a RPT device. Air from the RPT device is humidified in a humidifier 5000, and passes along an air circuit 4170 to the patient 1000.
Figure 1B:
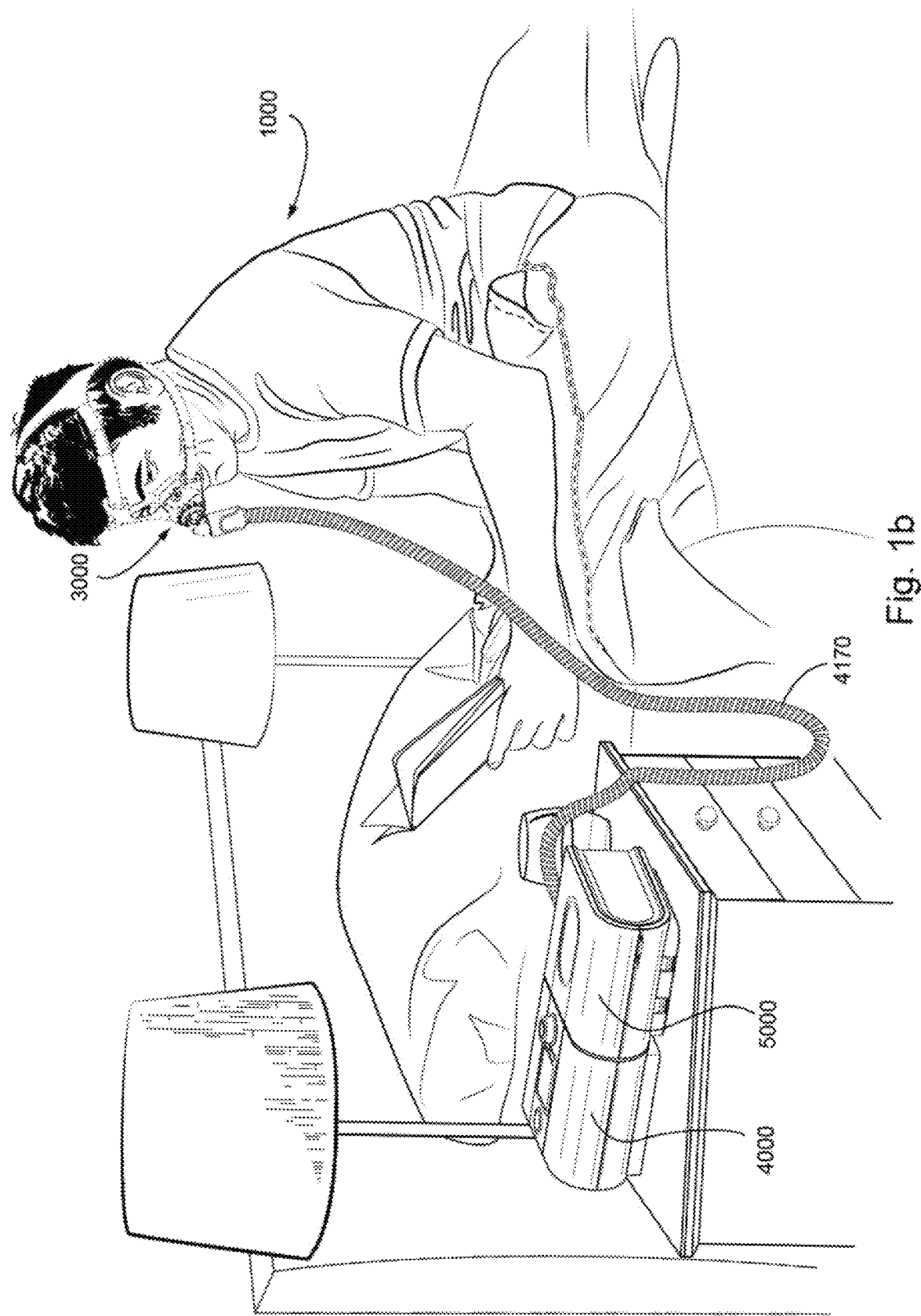
Figure 1C:

In one form, the plenum chamber 3200 may surround and/or be in fluid communication with the nares of the patient where the plenum chamber 3200 is a part of a nasal mask (e.g. shown in FIG. 1*b*). In another form, the plenum chamber 3200 may surround and/or be in fluid communication with the nares and the mouth of the patient where the plenum chamber 3200 is a part of a full-face mask (e.g., shown in FIG. 1*c*). In yet another form, the plenum chamber 3200 may engage and/or be in fluid communication with one or more of the nares of the patient where the plenum chamber 3200 is a part of nasal pillows (e.g., shown in FIG. 29).

4.3.3 Positioning and Stabilising Structure 3300

Preferably the seal-forming structure 3100 of the patient interface 3000 of the present technology is held in sealing position in use by the positioning and stabilising structure 3300.

4.4 RPT Device 4000

An example RPT device 4000 that may be suitable for implementing aspects of the present technology may include mechanical and pneumatic components 4100, electrical components 4200 and may be programmed to execute one or more of the control methodologies or algorithms described throughout this specification. The RPT device may have an external housing 4010, preferably formed in two parts, an upper portion 4012 of the external housing 4010, and a lower portion 4014 of the external housing 4010. In alternative forms, the external housing 4010 may include one or more panel(s) 4015. Preferably the RPT device 4000 comprises a chassis 4016 that supports one or more internal components of the RPT device 4000. In one form a pneumatic block 4020 is supported by, or formed as part of the chassis 4016. The RPT device 4000 may include a handle 4018.

The pneumatic path of the RPT device 4000 preferably comprises an inlet air filter 4112, an inlet muffler 4122, a controllable pressure device 4140 capable of supplying air at positive pressure (preferably a blower 4142), and an outlet muffler 4124. One or more pressure transducers 4272 and flow sensors 4274 are included in the pneumatic path.

The preferred pneumatic block 4020 comprises a portion of the pneumatic path that is located within the external housing 4010.

The RPT device 4000 preferably has an electrical power supply 4210, one or more input devices 4220, a central controller 4230, a therapy device controller 4240 and/or any of the controllers previously described, a pressure device 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

The central controller 4230 of the RPT device 4000, which may include one or more processors, can be programmed to execute one or more algorithm modules, preferably including a pre-processing module, a therapy engine module, a pressure control module, and further preferably a fault condition module. It may further include a vent control module that may be configured with one or more of the vent control methodologies described throughout this specification.

4.4.1 RPT Device Mechanical & Pneumatic Components 4100

4.4.1.1 Air Filter(s) 4110

A RPT device in accordance with one form of the present technology may include an air filter 4110, or a plurality of air filters 4110.

In one form, an inlet air filter 4112 is located at the beginning of the pneumatic path upstream of a blower 4142. See FIG. 4b.

In one form, an outlet air filter 4114, for example an antibacterial filter, is located between an outlet of the pneumatic block 4020 and a patient interface 3000. See FIG. 4b.

4.4.1.2 Muffler(s) 4120

In one form of the present technology, an inlet muffler 4122 is located in the pneumatic path upstream of a blower 4142. See FIG. 4b.

In one form of the present technology, an outlet muffler 4124 is located in the pneumatic path between the blower 4142 and a patient interface 3000. See FIG. 4b.

4.4.1.3 Pressure Device 4140

In a preferred form of the present technology, a pressure device 4140 for producing a flow of air at positive pressure is a controllable blower 4142. For example the blower may include a brushless DC motor 4144 with one or more impellers housed in a volute. The blower may be preferably capable of delivering a supply of air, for example about 120 litres/minute, at a positive pressure in a range from about 4 cmH$_2$O to about 20 cmH$_2$O, or in other forms up to about 30 cmH$_2$O.

The pressure device 4140 is under the control of the therapy device controller 4240.

4.4.1.4 Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

4.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

4.4.1.6 Air Circuit 4170

An air circuit 4170 in accordance with an aspect of the present technology is constructed and arranged to allow a flow of air or breathable gasses between the pneumatic block 4020 and the patient interface 3000.

4.4.1.7 Oxygen Delivery

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

4.4.2 RPT Device Electrical Components 4200

4.4.2.1 Power Supply 4210

In one form of the present technology power supply 4210 is internal of the external housing 4010 of the RPT device 4000. In another form of the present technology, power supply 4210 is external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000. The power supply may also optionally provide power to any actuator, controller and/or sensors for a vent arrangement as described throughout this specification

4.4.2.2 Input Devices 4220

In one form of the present technology, a RPT device 4000 includes one or more input devices 4220 in the form of buttons, switches or dials to allow a person to interact with the device. These may be implemented for entering settings for operation of the components of the RPT device such as the vent arrangement. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

4.4.2.3 Central controller 4230

In one form of the present technology, the central controller 4230 is a dedicated electronic circuit configured to receive input signal(s) from the input device 4220, and to provide output signal(s) to the output device 4290 and/or the therapy device controller 4240.

In one form, the central controller 4230 is an application-specific integrated circuit. In another form, the central controller 4230 comprises discrete electronic components.

In another form of the present technology, the central controller 4230 is a processor suitable to control a RPT device 4000 such as an x86 INTEL processor.

A processor of a central controller 4230 suitable to control a RPT device 4000 in accordance with another form of the present technology includes a processor based on ARM Cortex-M processor from ARM Holdings. For example, an STM32 series microcontroller from ST MICROELECTRONICS may be used.

Another processor suitable to control a RPT device 4000 in accordance with a further alternative form of the present technology includes a member selected from the family ARM9-based 32-bit RISC CPUs. For example, an STR9 series microcontroller from ST MICROELECTRONICS may be used.

In certain alternative forms of the present technology, a 16-bit RISC CPU may be used as the processor for the RPT device 4000. For example a processor from the MSP430 family of microcontrollers, manufactured by TEXAS INSTRUMENTS, may be used.

The processor is configured to receive input signal(s) from one or more transducers 4270, and one or more input devices 4220.

The processor is configured to provide output signal(s) to one or more of an output device 4290, a therapy device controller 4240, a data communication interface 4280 and humidifier controller 5250.

In some forms of the present technology, the processor of the central controller 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a RPT device 4000. However, in some forms of the present technology the processor(s) may be implemented discretely from the flow generation components of the RPT device 4000, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein. Similarly, such a processor may perform any of the methodologies described herein for purposes controlling operation of any vent arrangement described in this specification.

4.4.2.4 Clock 4232

Preferably RPT device 4000 includes a clock 4232 that is connected to processor.

4.4.2.5 Therapy Device Controller 4240

In one form of the present technology, therapy device controller 4240 is a pressure control module 4330 that forms part of the algorithms 4300 executed by the processor of the central controller 4230.

In one form of the present technology, therapy device controller 4240 is a dedicated motor control integrated circuit. For example, in one form a MC33035 brushless DC motor controller, manufactured by ONSEMI is used.

4.4.2.6 Protection Circuits 4250

Preferably a RPT device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

4.4.2.7 Memory 4260

In accordance with one form of the present technology the RPT device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, RPT device 4000 includes removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

4.4.2.8 Transducers 4270

Transducers may be internal of the device, or external of the RPT device. External transducers may be located for example on or form part of the air delivery circuit, e.g. the patient interface. External transducers may be in the form of non-contact sensors such as a Doppler radar movement sensor that transmit or transfer data to the RPT device.

4.4.2.8.1 Flow

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal representing total flow Qt from the flow transducer 4274 is received by the processor.

4.4.2.8.2 Pressure

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the central controller processor. In one form, the signal from the pressure transducer 4272 is filtered prior to being received by the central controller 4230.

4.4.2.8.3 Motor Speed

In one form of the present technology a motor speed signal 4276 is generated. A motor speed signal 4276 is preferably provided by therapy device controller 4240. Motor speed may, for example, be generated by a speed sensor, such as a Hall effect sensor.

4.4.2.9 Data communication systems 4280

In one preferred form of the present technology, a data communication interface 4280 is provided, and is connected to central controller processor. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor of central controller 4230. In another form, data communication interface 4280 is an integrated circuit that is separate from the central controller processor.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

4.4.2.10 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

4.4.2.10.1 Display Driver 4292

A display driver 4292 receives as an input the characters, symbols, or images intended for display on the display 4294, and converts them to commands that cause the display 4294 to display those characters, symbols, or images.

4.4.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

4.5 Communication and Data Management System

FIG. 7 depicts an example system 700 in which aspects of the disclosure may be implemented. This example should not be considered as limiting the scope of the disclosure or usefulness of the features described herein. In this example, system 700 includes server 710, patient devices 720, 730, and 740, storage systems 750, as well as computing device 760. These devices may each communicate over network 4282. System 700 may be scaled to any size network. For example, while only three patient devices 720, 730, and 740 are shown, system 700 may include any number of patient devices.

Each patient device 720, 730, and 740 may include one or more devices, including RPT 4000, humidifier 5000, and patient interface 3000. In addition, each patient device 720, 730, and 740 may be operated at remote locations and by different patients. While only controller 4230 and memory 4260 are shown in patient device 720, each patient device may include any of the components discussed above in connection with RPT 4000, humidifier 5000, and patient interface 3000. In addition, while patient devices 720, 730, and 740 are shown as communicating directly with the server 710 or the computing device 760 over 4282, each patient device may also communicate over network 4282 via an external computing device (not shown). For example, patient device 720 may communicate with a personal computer that transmits data over network 4282.

Servers 710 may contain one or more processors 712, memory 714 and may be incorporated with other components typically present in general purpose computing devices. Memory 714 of server 710 may store information accessible by processor 712, including instructions 715 that can be executed by the processor 712. Memory 714 may also include data 718 that can be retrieved, manipulated or stored by processor 712. The memory can be of any non-transitory type capable of storing information accessible by the processor. The instructions 716 may include instructions that are directly or indirectly executed by processor 712. In that regard, the terms "instructions," "application," "steps" and "programs" can be used interchangeably herein. Functions, methods and routines of the instructions are explained in more detail below.

Data 718 may be retrieved, stored or modified by processor 712 in accordance with the instructions 716. For instance, although the subject matter described herein is not limited by any particular data structure, the data can be stored in computer registers, in a relational database as a table having many different fields and records, or XML documents. Data 718 may also be any information sufficient to identify or calculate relevant information, such as numbers, descriptive text, proprietary codes, pointers, references to data stored in other memories such as at other network locations. The one or more processors 712 may include conventional processors, such as a CPU, or may be a hardware-based component, such as an ASIC.

Although FIG. 7 functionally illustrates the processor, memory, and other elements of server 710, computing device 760 and patient devices 720, 730, and 740 as each being within one block, the various components of each device may be stored within the different physical housings. For example, memory 714 may be a hard drive or other storage media located in a housing different from that of server 710. Similarly, processor 712 may include a plurality of processors, some or all of which are located in a housing different from that of server 710. Accordingly, references to a processor, computer, computing device, or memory will be understood to include references to a collection of processors, computers, computing devices, or memories that may or may not operate in parallel. Although some functions are described herein as taking place on a single computing device having a single processor, various aspects of the disclosure may be implemented by a plurality of computing devices communicating information with one another, such as by communicating over network 4282.

In many instances, it is preferable for patient devices 720, 730, and 740 to communicate with network 4282 using wireless communication. However, network 4282 and intervening nodes described herein can be interconnected using various protocols and systems, such that the network can be part of the Internet, World Wide Web, specific intranets, wide area networks, local networks, or cell phone networks. The network can utilize standard communications protocols, such as Ethernet, Wi-Fi and HTTP, protocols that are proprietary to one or more companies, and various combinations of the foregoing. Although certain advantages are obtained when information is transmitted or received as noted above, other aspects of the subject matter described herein are not limited to any particular manner of transmission of information.

Servers 710 may include one or more communication servers that are capable of communicating with storage system 750, computing device 760, and patient devices 720, 730, and 740 via network 4282. As will be described in greater detail below, servers 710 may transmit updates 716 of software and firmware over network 4282 to patient devices 720, 730, and 740. In turn, patient devices 720, 730, and 740 may transmit data to server 710 in accordance with software and firmware in the form of the instruction sets 726.

The computing device 760 may be configured similarly to the server 710, with one or more processors 762, memory 764 and instructions as described above. Each such computing device may be a personal computing device intended for use by a clinician and have all of the components normally used in connection with a personal computing device such as a central processing unit (CPU), memory (e.g., RAM and internal hard drives) storing data and instructions, a display such as a display 766 (e.g., a monitor having a screen, a touch-screen, a projector, a television, or other device that is operable to display information), and user input device 768 (e.g., a mouse, keyboard, touch-screen or microphone).

4.6 Example Methods

As discussed above, each patient device 720, 730, and 740 shown in FIG. 7 may include one or more medical devices, including RPT 4000, humidifier 5000, and patient interface 3000. In performing the operations described above, patient devices 720, 730, and 740 may implement instruction sets 726, which may include software or firmware. As discussed above in connection with FIG. 4c, RPT 4000 may include multiple controllers, such as humidifier controller 5250 and therapy device controller 4240. Each of these controllers may operate in connection with a specific instruction set 726. Accordingly, each instruction set may relate to a specific component of the patient device, including the components discussed above. For example, returning to FIG. 7, patient device 720 is shown as including a number of modules, including communications module 721, humidifier module 723, and alarm module 725. Each of these modules may access and implement a distinct instruction set 726. In another example, a particular instruction set 726 may be implemented by more than one module, including any of the modules discussed above.

As patient devices 720, 730, 740 are used by their respective patients, updates to instruction sets 726 may become available and necessary. Such updates may be associated with improving specific functions or fixing identified problems with operational aspects of one or more modules of the device. Thus, in some instances an update may be essential for the efficient administration of the patient treatment and even for the safety of the patient. In accordance with one aspect of the disclosure, one or more instruction sets 726 may be automatically updated over communication network 4282. In particular, servers 710 may transmit one or more instruction set updates 716 to one or more of the patient devices 720, 730, and 740. Upon receiving an instruction set update 716, each patient device 720, 730, and 740 may alter instruction sets 726 in a manner indicated by the transmitted instruction set update 716. In this way, patient device may be easily upgraded and otherwise customized remotely, without requiring a patient to bring the patient device to a clinician or to a service center.

In one aspect, specific patient devices may be selected as being able to receive, or otherwise suitable to receive, a particular update. For example, server 710 may determine that patient device 720 should receive a particular instruction set update 716, while patient devices 730 and 740 should not. In order to identify the specific patient device that will receive a particular update, server 710 may maintain configuration data 718 for each patient device 720, 730, and 740. Configuration data 718 may include any information that may be used to identify a particular patient device, including a serial number, identification of the software and firmware versions that are currently being implemented by the patient device, and hardware version numbers. Configuration data 718 may also include a record of the instruction set updates that have previously been transmitted to a patient device and an indication of whether each transmitted instruction set update was successfully or unsuccessfully applied to patient device. In addition, configuration data 718 is not limited to information that is distinct with respect to one particular patient device but may include information that is applicable to a number of patient devices. For example, configuration data 718 may include identification of the patient device's supplier or retailer, as well as the location or region in which the patient device is being used. Alternatively, an update may be triggered by other factors, such as a fault condition that can be fixed by a specific update.

Configuration data 718 may be provided by the patient devices 720, 730, and 740 through a registration process. For example, patient device 720 may transmit configuration data 728 over network 4282 to server 710. Server 710 may then store the received configuration data 728 in memory 714 as configuration data 718. Registration of a patient device's configuration data 718 may occur upon the patient's initial use of the patient device. In addition, configuration data 718 may be updated on server 710 upon any change that occurs in the configuration data 728. For example, patient device 720 may transmit a notification to server 710 that it has successfully updated the firmware for its humidifier module 723 from a first version to a second version. Server 710 may then update configuration data 718 so as to indicate that patient device 720 is currently implementing the second version of the humidifier module firmware. In one example, patient device 720 may check its current configuration data 728 each time it is started and report any changes in configuration data 728 to server 710.

In accordance with one aspect, a user of computing device 760 may select particular patient devices to update by communicating with server 710. For example, a user of computing device 760 may access a website that provides an interface with server 710 by which computing device 760 may designate a particular update 716 for particular patient devices 720, 730 and 740. In order to identify the patient devices for which an update should be performed, computing device 760 may search memory 714 of server 710 for patient devices that meet certain criteria. For example, a user of computing device 760 may request that server 710 identify all patient devices that are implementing a specific software version or have a serial number within a particular range. In another example, computing device 760 may request a list of all patient devices that have been purchased from a particular retailer.

The user of the computing device 760 may identify, via server 710, the patient devices that are to be updated. If there are more than one possible updates, the user may also have to identify or select the specific update 716 to be provided to the patient devices. In identifying a particular update, the user may identify which components of the patient devices are to be updated, as well as the particular version of the software or firmware that is to be implemented by the component. For example, the user of computing device 760 may request that server 710 provide patient devices 720 and 730 with an update 716 for humidifier module 723 and that the update be for version 3.1 of humidifier firmware. Server 710 may then transmit the selected update 716 to patient devices 720 and 730. Version 3.1 of the firmware may include new or different settings than the settings being currently implemented by patient devices 720 and 730. These new settings may be implemented once patient devices 720 and 730 have installed version 3.1 of the firmware. While the process of selecting an update 716 and transmitting the selected update 716 may be performed by a single server 710, it may alternatively be performed by more than one server 710. For example, computing device 760 may make an update request with a communications server. The communications server may then transmit the request to a download server that, in turn, transmits the selected update to the designated patient devices.

The instruction update data may also include any one of the following; data specifying where to get the instruction update from, e.g. host server, port, filename; the schedule time for performing the update for each device so that large volumes of device updates can be effectively managed; whether or not to request the patient to confirm that the update should be applied; instructions for the update not be applied until patient treatment is stopped, if applicable; data structure and functionality enabling cancelling upgrades that have not yet occurred, if necessary; a batch capability to request bulk upgrades in a single operation as well as the ability to check the status of these upgrades afterwards in a single operation indicating which upgrades in the list succeeded, which failed, which have not started etc.

In providing updates 716 to patient devices 720, 730 and 740, server 710 may also transmit verification data that can be used to verify that the update has been downloaded successfully. Each update 716 may include verification data. The verification data may take the form of a checksum, a cyclic redundancy check, or identification of the size of the update file. For example, server 710 may transmit to patient device 720 an update 716 that includes a checksum. Patient device 720 may compare the checksum against the received update 716 to determine if the entire update has been received. If the downloaded update matches the checksum, patient device may install the update and transmit an indication to server 710 that installation was successful. However, if the downloaded update does not match the checksum, patient device may not install the update and may transmit an indication to server 710 that installation did not occur.

A transmission from server 710 to patient device 720 may include an update for more than one component. For example, a particular update 716 may be transmitted from server 710 to patient device 720 that modifies multiple instruction sets 726 for multiple components, such as instruction sets 726 for communications module 721 and humidifier module 723. In another example, a particular instruction set 726 may be implemented by multiple components, so that a modification of that instruction set 726 causes a modification of those multiple components. Multiple updates may also be transmitted and applied to a single patient device 720. If multiple updates 716 are included in a transmission, server 710 may identify the order in which the updates are to occur. The patient device in receipt of the transmission may then implement the updates 716 in accordance with the order designated by server 710. A single component of the patient device may need to be updated more than once, in order for the final version of the instruction set to be implemented. For example, patient device 720 may need to download and install version 2.0 of an instruction set before version 3.0 may be installed. Accordingly, configuration data 718 may include identification of patient devices 720, 730 and 740 that are currently capable of installing a particular update 716, as well as identification of other updates that must be installed in order for the particular update 716 to be installed. In another example, a transmitted update 716 may include an identification of the version or versions of instruction sets 726 that are needed in order for update 716 to be installed. Prior to installing update 716, patient device 720 may compare the required versions identified in update 716 with the version that it is currently implementing. Patient device 720 may avoid installing update 716 if patient device 720 is not currently implementing one of the required versions.

Patient device 720 may determine whether it satisfies a specified build standard identified by update 716, and perform or avoid installation of update 716 based on the determination. For example, the identified build standard may include the combination of components that are needed for the update to be installed. Patient device 720 may determine whether it meets the identified build standard, such as by determining if it is using the identified combination of components. If the identified components are being used by patient device 720, those components may be updated in accordance with update 716. However, patient device 720 may avoid installing update 716 if patient device 720 does not contain one or more of the identified components. In one example, patient device 720 may avoid installing only the portions of update 716 that relate to the components that patient device 720 does not contain or use, but proceed with installing other portions of update 716.

In accordance with one aspect, the patient devices may be updated in accordance with a schedule. For example, a user of computing device 760 may provide server 710 with a schedule of updates, such as by identifying the dates on which particular patient devices are to receive particular updates 716. Server 710 may then transmit updates 716 in accordance with the schedule. In one example, the schedule may be incorporated into the configuration data 718 for each patient device. In this way, an update that applies to a large number of patient devices may be applied over an extended period of time, such as over a period of weeks or months, in order to decrease the load that network 4282 must transmit at any given time. When a patient device is scheduled to receive an update 716, server 710 may transmit an update request. The update request may take the form of an SMS message or some other shoulder tap transmission. Upon receiving the update request from server 710, patient device 720 may respond with an indication that it is prepared to receive the update. The update may then be transmitted to and installed by patient device 720. Server 710 may also cancel updates 716 that are scheduled to occur. For example, a user of computing device 760 may send a request that a particular update 716 be cancelled for one or more patient devices 720, 730, and 740. In response to the request of computing device 760, server 710 may remove the particular update 716 from a list of scheduled updates. If the update has already been transmitted to one or more of the patient devices, but not yet installed, server 710 may transmit au update cancellation to the one or more patient devices. Upon receiving the update cancellation, patient devices 720, 730, and 740 may delete the received update 716 from memory before it is installed.

Alternatively, the transmission may occur on a specific suitable day, but the respective device may be instructed to implement the update on a specific later date. After receiving an update from server 710, patient device 720 may wait before installing the update for various reasons. For example, if a patient is receiving treatment from patient device 720 when the update is received, patient device 720 may wait until the patient's treatment has ended before installing the update. This may prevent a patient's therapy from being interrupted or otherwise negatively affected by the installation of the update. In one aspect, the update may indicate whether it may be installed while the patient device is being used. In particular, the update may indicate specific operations that may be performed by the patient device while the update is being performed. For example, update 716 may relate solely to communications module 721, which does not relate to operations that are performed while the patient device provides respiratory therapy. Accordingly, update 716 may indicate that it may be installed while patient device 720 is being used to provide respiratory therapy. During installation, patient device 720 may display a notice indicating that patient device 720 is being updated. The notice may include displaying a message stating that the patient should not turn off the patient device and that the patient should wait until the update has been completed before using the patient device in particular manners. In one example, patient device 720 may require confirmation from the patient before an update is installed. Also, new software may be downloaded by many devices over a period of time, however the downloaded update can be installed on all devices at the same day for marketing or communication purposes.

In accordance with one aspect, a user of computing device 760 may query server 710 for the status of updates 716. For example, computing device 760 may request identification of those patient devices that have not received or have not yet installed a particular update 716. In addition, computing device 760 may request a list of all patient devices for which one or more updates 716 have been installed, as well as information regarding any errors that have occurred in connection with the transmission and installation of updates 716. In addition, server 710 may provide computing device 760 with a list of current instruction sets, such as versions of software and firmware, that particular patient devices are currently implementing. For example, computing device 760 may query server 710 for a list of instruction sets 726 being implemented by patient device 720. Sever 710 may access configuration data 718 in order to identify the queried information and transmit the information to computing device 760. Computing device 760 may make the query and receive the queried information from server 710 by accessing a website or some other server interface. Server 710 may require that computing device 760 provide identification information or a password in connection with the query, so as to maintain the confidentiality of patient information.

FIG. 8 shows a flow diagram 800 that may be performed by a patient device, such as patient device 720 of system 700. As described above, a patient device may store and implement sets of instructions. In block 802, the patient device may implement a set of instructions, such as software or firmware that is currently accessible to the patient device. The set of instructions may relate to the operation of a plurality of components within the patient device and need not be stored at a single location. In implementing the set of instructions, the patient device may transmit data over a network to one or more external devices (Block 804). For example, patient device 720 may transmit, over network 4282, data relating to a patient's use of patient device 720 in accordance with one or more sets of instructions. This transmission may include information about the dates and times for which the patient has used the patient device. The patient device may also receive transmissions from external devices, such as server 710, and may determine whether the received transmission is related to an update to one or more instruction sets. (Block 806). For example, the patient device may receive a transmission indicating that update data may be accessed at a particular location, such as at a particular address of a server. If no update has been received, the patient device may continue to implement the current instruction set (Block 802). If an indication of an update is received, the patient device may receive the update data, such as by requesting or accessing update files at an identified address.

The patient device may determine if there is an error in relation to the update data (Block 808). For example, as described above, patient device may compare the update with a checksum to determine that the entire update has been received. In addition, patient device may determine whether the version of the instruction set that it is currently implemented matches one of the versions that are needed in order for the update to be installed. If it is determined that an error exists in relation to the update, the patient device may transmit an error notification (Block 810). For example, patient device 720 may transmit a notification to server 710 indicating that the update did not match the checksum that was provided. The notification may also include a request for the update to be retransmitted.

If no error is detected in relation to the update, the patient device may install the update (Block 812). As described above, the update may include modifying one or more sets of instructions. The modification may include deleting a portion of an instruction set and adding to the instruction set, as well as replacing an original instruction set with an entirely new instruction set. As set forth above, an update may include modifications to various instruction sets, including instruction sets for different components of the patient device. Upon installing the update, the patient device may perform a check to determine if the installation was successful, including performing a check of each updated component (Block 814). If the installation was not successful, the patient device may transmit an error notification (Block 810). In addition the patient device may revert back to and implement the original instruction set in accordance with Block 802. If installation is determined to be successful, the patient device may transmit a notification to an external device, such as server 710, indicating that the update has been installed (Block 816). The patient device may also access and implement the current instruction sets, including the updated instruction sets, in accordance with Block 802.

FIG. 9 shows flow diagram 900 that may be performed by computing devices of the disclosed system, including server 710 of system 700. In Block 902, a server may receive a query for identification of patient devices that meet one or more criteria. For example, as described above, server 710 may receive a query from computing device 760. This query may seek identification of all patient devices that meet one or more criteria provided by a user of computing device 760. The criteria may be based on any number of aspects or features of the patient device, such the region in which the patient device is located, the patient device's serial numbers, as well as software and firmware versions that are currently being implemented by the patient device. The server may access configuration data in response to the received query (Block 904), and may respond to the query by transmitting data that identifies the patient devices for which the identified criteria are met (Block 906).

The server may then receive a request for one or more updates to be transmitted to one or more patient devices (Block 908). For example, as described above, computing device 760 may receive a list from server 710 of patient devices 720, 730 and 740 that meet criteria provided by the user of computing device 760. The user may then select specific updates 716 to be transmitted to patient devices 720, 730, and 740. Upon receiving the request of Block 908, the server may access update data (Block 910) and transmit the update data to the patient devices identified in the received request (Block 912). The functions in items 902-908 may be implemented in a different order. For example, the server may receive the request for identifying devices with specific configurations at the same time (or even before) it receives the update request and send the updates only to the devices that fulfil the specified criteria. In addition, Block 910 need not be performed in order for the update data to be transmitted to the patient device in accordance with Block 912. For example, server 710 may transmit update data as an address that indicates the location of where the update files are stored. The location identified by the address may be on server 710 or elsewhere. In this way, the address for update files may be provided to the patient device without requiring server 710 to access the actual update file data that is stored at the identified location.

The server may also determine if the transmission and/or installation of the update was successful (Block 914). For example, the server may receive from each patient device either an error notification or a message that the update was successfully installed. If an error occurred in the transmission of the update, the server may transmit the update data again for each patient device for which the error occurred (Block 912). Alternatively, the actual update file (new software) can be requested by the treatment device itself from the file server, rather than being pushed by server 710 down to the device. The update of a patient device may not occur immediately, in that the update may be contingent on the occurrence of one or more conditions. For example, the update data may indicate that the patient device is to install the update after the device has provided treatment for a period of 200 hours. Accordingly, a substantial amount of time may lapse between Block 912 and Block 914. However, if the transmission and installation are successful, the server may revise the stored configuration data to indicate that the one or more patient devices are currently implementing instruction sets that correspond to the transmitted updates (Block 916) and report that the update was successful (Block 918). For example, if the one or more of the patient devices have been successfully updated, server 710 may transmit a message to computing device 760 to notify a user, such as technical personnel, that the update is complete. This message may identify the specific patient devices, or group of patient devices, that have successfully installed the update.

While the operations set forth in FIGS. 8 and 9 may each be performed by a single device, the operations may alternatively be performed by more than one device. For example, a patient device may communicate with a personal computer over a wireless network, so that the personal computer may perform one or more of the operations described above. The server referenced in connection with FIGS. 8 and 9 may also include a plurality of servers. Regarding the specific operations shown in FIGS. 8 and 9, various operations may be added or removed from flow diagrams 800 and 900. In addition, various operations need not be performed in the same order as set forth in flow diagrams 800 and 900. For example, the server may transmit update information to the treatment devices indicating what update is required, where to obtain it (host, port, filename) and how to verify it (e.g. checksum/CRC). The treatment device comms module may then requests the update file (instructions) from the specified host (server). This slightly different functional diagram allows distributing the load of downloading large volumes of software over many servers if necessary i.e. not just from Server 710, as shown in the FIG. 7. In addition, the treatment device can re-request the update file (i.e. the new software) from the specified server itself if there is a transmission error without interaction with server 710. It is also possible that the server, upon being notified of an error, could re-try the operation as described above.

4.7 Glossary

In certain forms of the present technology, one or more of the following definitions may apply. In other forms of the present technology, alternative definitions may apply.

4.7.1 General

Air: Air will be taken to include breathable gases, for example air with supplemental oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

4.7.2 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

4.7.3 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a patient interface plenum chamber will be taken to mean a portion of a patient interface having walls enclosing a volume of space, such as for a full-face mask (e.g., nose and mouth mask), a nasal mask or a nasal pillow, the volume having air therein pressurised above atmospheric pressure in use by the patient. A shell may form part of the walls of a patient interface plenum chamber. In one form, a region of the patient's face abuts one of the walls of the plenum chamber, such as via a cushion or seal.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

4.8 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

LIST OF REFERENCE NUMBERS communications system 700
server 710
processor 712
memory 714
instructions 715
instruction set update 716
configuration data 718
patient device 720
communications module 721
humidifier module 723
alarm module 725
instruction set 726
configuration data 728
patient device 720
patient device 730
patient device 740
storage system 750
computing device 760
processor 762
memory 764
display 766
user input device 768
patient 1000
patient interface 3000
Seal-forming structure 3100
plenum chamber 3200
perimeter 3210
position and stabilising structure 3300
vent 3400
connection port 3600
RPT device 4000
external housing 4010
upper portion of external housing 4012
lower portion of external housing 4014
panel 4015
chassis 4016
handle 4018
pneumatic block 4020
pneumatic component 4100
air filter 4110
inlet air filter 4112
outlet air filter 4114
muffler 4120
inlet muffler 4122
outlet muffler 4124
pressure device 4140
blower 4142
motor 4144
brushless DC motor 4144
back valve 4160
air circuit 4170
supplemental oxygen 4180
electrical component 4200
board assembly PCBA 4202
power supply 4210
input device 4220
central controller 4230
clock 4232
therapy device controller 4240
protection circuit 4250
memory 4260
transducer 4270
pressure transducer 4272
flow sensor 4274
motor speed signal 4276
data communication system 4280
remote external communication network 4282
local external communication network 4284
remote external device 4286
local external device 4288
output device 4290
display driver 4292
display 4294
algorithm 4300
pressure control module 4330
humidifier 5000
humidifier controller 5250

The invention claimed is:

1. A method for updating a patient device for providing medical treatment, the method comprising:
   accessing, by one or more processors of one or more servers, configuration data relating to a plurality of patient devices, wherein the plurality of patient devices each implement a set of instructions and the configuration data includes a record of instruction updates that have previously been transmitted to each patient device of the plurality of patient devices and an indication of whether each transmitted instruction update was successfully or unsuccessfully applied to each patient device;

identifying, by the one or more processors of the one or more servers, one or more patient devices, from the plurality of patient devices, that should be updated, wherein the identifying is based on determining which of the plurality of patient devices has configuration data that meets one or more criteria;

transmitting, by the one or more processors of the one or more servers, an instruction update to the one or more patient devices;

receiving, by the one or more processors of the one or more servers, from each of the one or more patient devices an indication that an updated patient device component has been checked; and based on the received indication that the updated patient device component has been checked, updating, by the one or more processors of the one or more servers, the configuration data for each of the one or more patient devices that has installed the instruction update.

2. The method of claim 1, wherein the instruction update is selected by the one or more processors of the one or more servers, from a plurality of instruction updates, based on the configuration data.

3. The method of claim 1, wherein the one or more criteria and the instruction update are selected based on one or more transmissions received from a remote computing device.

4. The method of claim 1, wherein the instruction update includes at least one of the following:
data specifying a location of an instruction update file;
instructions as to which component of the patient device should the instruction update be applied to;
schedule time for performing the instruction update for each patient device;
instructions on whether or not to request confirmation that the instruction update should be applied;
data structure and functionality enabling cancelling upgrades that have not yet occurred;
batch capability to request bulk upgrades in a single operation; and
an ability to check a status of these upgrades in a single operation indicating the status of the upgrades.

5. The method of claim 1, wherein the instruction update comprises instructions for updating one or more operations of the one or more patient devices, wherein the one or more operations comprise control of a pressure device for producing a flow of air at positive pressure.

6. The method of claim 1, wherein the plurality of patient devices are respiratory pressure therapy devices.

7. The method of claim 1, wherein transmitting the instruction update further comprises transmitting verification data, wherein the verification data is used by the patient device to verify that the instructions update was successfully downloaded.

8. The method of claim 1, further comprising receiving, by the one or more processors of the one or more servers, an indication from each of the one or more patient devices whether the instruction update has been installed.

9. The method of claim 8, further comprising retransmitting, by the one or more processors of the one or more servers, the instruction update to each patient device for which it is determined that the instruction update was not successfully installed.

10. The method of claim 1, wherein the configuration data comprises at least one of a) a serial number, b) a version of the set of instructions that is currently installed on the patient device, c) a hardware version, and d) a region in which the patient device is being used.

11. A system comprising one or more servers with one or more processors for updating a patient device in providing medical treatment, the one or more servers being configured to:
access configuration data relating to a plurality of patient devices, wherein the plurality of patient devices each implement a set of instructions and the configuration data includes a record of instruction updates that have previously been transmitted to each patient device of the plurality of patient devices and an indication of whether each transmitted instruction update was successfully or unsuccessfully applied to each patient device;
identify one or more patient devices, from the plurality of patient devices, that should be updated, wherein the identifying is based on determining which of the plurality of patient devices has configuration data that meets one or more criteria;
transmit an instruction update to the one or more patient devices;
receive from each of the one or more patient devices an indication that an updated patient device component has been checked; and
based on the received indication that the updated patient device component has been checked, update the configuration data for each of the one or more patient devices that has installed the instruction update.

12. The system of claim 11, wherein the one or more servers are configured to select the instruction update, from a plurality of instruction updates, based on the configuration data.

13. The system of claim 11, wherein the one or more servers are configured to receive one or more transmissions from a remote computing device, and select the one or more criteria and the instruction update based on the received one or more transmissions.

14. The system of claim 11, wherein the instruction update includes at least one of the following:
data specifying a location of an instruction update file;
instructions as to which component of the patient device should the instruction update be applied to;
schedule time for performing the instruction update for each patient device;
instructions on whether or not to request confirmation that the instruction update should be applied;
data structure and functionality enabling cancelling upgrades that have not yet occurred;
batch capability to request bulk upgrades in a single operation; and
an ability to check a status of these upgrades in a single operation indicating the status of the upgrades.

15. The system of claim 11, wherein the instruction update comprises instructions for updating one or more operations of the one or more patient devices, wherein the one or more operations comprise control of a pressure device for producing a flow of air at positive pressure.

16. The system of claim 11, wherein the plurality of patient devices are respiratory pressure therapy devices.

17. The system of claim 11, wherein the one or more servers are configured to transmit verification data, wherein the verification data is used by the patient device to verify that the instructions update was successfully downloaded.

18. The system of claim 11, wherein the one or more servers receive an indication from each of the one or more patient devices whether the instruction update has been installed.

19. The system of claim 18, wherein the one or more servers are configured to retransmit the instruction update to each patient device for which it is determined that the instruction update was not successfully installed.

20. The system of claim 11, wherein the configuration data comprises at least one of a) a serial number, b) a version of the set of instructions that is currently installed on the patient device, c) a hardware version, and d) a region in which the patient device is being used.

21. A method for updating a patient device for providing medical treatment, the method comprising:

accessing, by one or more processors, a first set of instructions for operation of the patient device;

performing, by the one or more processors, a first set of operations in accordance with the first instruction set;

receiving, by the one or more processors, an instruction update from a remote computing device over a network, wherein the instruction update is received based on the patient device being one of a plurality of patient devices having configuration data that meets one or more criteria, wherein the configuration data includes a record of instruction updates that have previously been transmitted to each patient device of the plurality of patient devices and indications of whether transmitted instruction updates were successfully and unsuccessfully applied to the plurality of patient devices;

updating, by the one or more processors, the first set of instructions in accordance with the instruction update so as to generate an updated set of instructions;

generating, by the one or more processors, an indication that an updated patient device component has been checked;

transmitting, by the one or more processors, confirmation to the remote computing device that an update of the first set of instructions has occurred, the transmitting including the generated indication that the updated patient device component has been checked; and performing, by the one or more processors, a second set of operations in accordance with the updated set of instructions.

* * * * *